US011605449B2

(12) United States Patent
Celka et al.

(10) Patent No.: US 11,605,449 B2
(45) Date of Patent: Mar. 14, 2023

(54) SYSTEMS AND METHODS FOR PARALLEL EXECUTION OF PROGRAM ANALYTICS UTILIZING A COMMON DATA OBJECT

(71) Applicant: Optum, Inc., Minnetonka, MN (US)

(72) Inventors: Chris Celka, Suwanee, GA (US); Cristian Robinson Rojas, San Diego, CA (US); Gogi Kshitij Singh, Buffalo Grove, IL (US); Jothi Sudhagar Ravindran, Naperville, IL (US); Mayank Kumar, Noida (IN)

(73) Assignee: Optum, Inc., Minnetonka, MN (US)

( * ) Notice: Subject to any disclaimer, the term of this patent is extended or adjusted under 35 U.S.C. 154(b) by 0 days.

(21) Appl. No.: 17/450,631

(22) Filed: Oct. 12, 2021

(65) Prior Publication Data

US 2022/0027343 A1 Jan. 27, 2022

Related U.S. Application Data

(63) Continuation of application No. 16/225,258, filed on Dec. 19, 2018, now abandoned.

(51) Int. Cl.
*G16H 10/60* (2018.01)
*G06Q 40/08* (2012.01)
*G06F 16/174* (2019.01)

(52) U.S. Cl.
CPC ......... *G16H 10/60* (2018.01); *G06F 16/1744* (2019.01); *G06Q 40/08* (2013.01)

(58) Field of Classification Search
None
See application file for complete search history.

(56) References Cited

U.S. PATENT DOCUMENTS

| 9,779,407 | B2 * | 10/2017 | Adjaoute | G06Q 40/08 |
| 2007/0294104 | A1 | 12/2007 | Boaz et al. | |
| 2013/0006655 | A1 * | 1/2013 | Van Arkel | G06Q 10/10 |
| | | | | 705/2 |

(Continued)

FOREIGN PATENT DOCUMENTS

| WO | 2016/029272 A1 | 3/2016 | |
| WO | WO-2016029272 A1 * | 3/2016 | G16H 40/67 |

OTHER PUBLICATIONS

SCIO Health Analytics, Predicting and Preventing Claim FWA with Advanced Profiling & Analytics (Year: 2016).*

(Continued)

*Primary Examiner* — Rachelle L Reichert
(74) *Attorney, Agent, or Firm* — Alston & Bird LLP

(57) ABSTRACT

An analytics platform for analyzing medical claims with low latency is configured to compress medical claims records into common data input objects that may be usable by a plurality of independent and parallel program analytics. The common data input objects are then passed as input to all of those program analytics, which are then configured to retrieve at least one compressed parameter file for use in processing data elements of the common data input object in accordance with a framework of a respective program analytic. The program analytics generate respective outputs based at least in part on data elements of the common data input objects, and the analytics platform combines those outputs into a single combined common output object.

20 Claims, 12 Drawing Sheets

(56) References Cited

U.S. PATENT DOCUMENTS

| | | | |
|---|---|---|---|
| 2014/0149128 A1 | 5/2014 | Getchius | |
| 2015/0332003 A1 | 11/2015 | Stamm et al. | |
| 2016/0117778 A1 | 4/2016 | Costello et al. | |
| 2016/0342751 A1* | 11/2016 | Alstad | G16H 40/20 |
| 2017/0017760 A1 | 1/2017 | Freese et al. | |
| 2017/0270435 A1 | 9/2017 | Gallardo | |
| 2018/0096105 A1* | 4/2018 | Bleicher | G06F 3/0484 |

OTHER PUBLICATIONS

"Healthcare Provider Fraud (IBM Case Manager, i2, Watson Content Analytics)," [YouTube Video], [online], [retrieved May 2, 2019], retrieved from the Internet <URL: https://www.youtube.com/watch?v=FdXIZ95xF40>.

"Predicting and Preventing Claim FWA With Advanced Profiling & Analytics," SCIO Health Analytics, Sep. 15, 2016, 27 pages, [online], [retrieved May 2, 2019], retrieved from the Internet <https://www.slideshare.net/SCIOhealthanalytics/predicting-and-preventing-claim-fwa-with-advanced-profiling-analytics>.

Botelho et al., "Combining Social Network Analysis With Semi-Supervised Clustering: A Case Study on Fraud Detection," 7 pages, [online], [retrieved May 2, 2019], retrieved from the Internet <URL: https://pdfs.semanticscholar.org/4f99/8cfdf338173ad0d413e04856cdff46c1f7da.pdf?_ga=2_9591351.343312097.1531436362-274940538.1513027392>.

Greene, "Practical Social Network Analysis With Gephi," Insight, pp. 1-23, [online], [retrieved May 2, 2019], retrieved from the Internet <URL: derekgreene.com/slides/derekgreene_gephi_slides.pdf>.

Kaplan, "Social Network Analysis-Extracting Its Potential in Heal Care Fraud Detection," European Healthcare fraud & Corruption Network, Oct. 2011, 31 pages.

Kavur, "Fighting Fraud With Social Network Analysis," CIO From IDG, Dec. 2, 2009, 11 pages, [online], [retrieved from the Internet May 2, 2019] <URL: https://www.cio.com/article/2422376/fighting-fraud-with-social-network-analysis.html>.

Liu et al., "Graph Analysis for Detecting Fraud, Waste, and Abuse in Healthcare Data," AAAI Publications, Twenty-Seventh IAAI Conference, Mar. 4, 2015, pp. 3912-3919, [online], [retrieved May 2, 2019], retrieved from the Internet <URL: https://www.aaai.org/ocs/index.php/IAAI/IAAI15/paper/view/9705/9888>.

* cited by examiner

SYSTEMS AND METHODS FOR PARALLEL EXECUTION OF PROGRAM ANALYTICS UTILIZING A COMMON DATA OBJECT

CROSS-REFERENCE TO RELATED APPLICATIONS

This application is a continuation of U.S. application Ser. No. 16/225,258 filed Dec. 19, 2018, which is hereby incorporated herein in its entirety by reference.

BACKGROUND

Often times data result outputs for consumption by businesses or other entities are combinations of data results generated by a number of different executable programs, and each of those executable programs have different data input requirements for execution.

Particularly in big data type environments, where input data for multiple executable programs encompass massive quantities of continually updating data, a need continually exists for systems and methods for processing such data while minimizing the amount of processing resources required.

BRIEF SUMMARY

To minimize the amount of processing resources required for generating a complex data result object, various embodiments utilize one or more compression algorithms for compressing data inputs into a common data input object having format consumable by a plurality of program analytics configured for parallel execution based at least in part on the common data input object. Certain of those program analytics may be configured for identifying abnormal data within the common data input object, and the abnormality criteria may be defined within those program analytics based at least in part on compressed historical data defining data norms.

Various configurations are particularly suitable for use in conjunction with a fraud, waste, abuse, and/or error detection system utilized in the healthcare industry. The program analytics executing in parallel may each be configured to utilize a common data input object, which was originally generated based at least in part on data of a healthcare claim, as input and may be configured for generating data output indicative of whether particular aspects of the underlying healthcare claim are suggestive of the presence of fraud or waste, given an appropriate context (e.g., historical context) for the data. As a specific example, one program analytic may be configured for scoring aspects of a particular healthcare claim to determine whether characteristics of the healthcare claim are indicative of fraud, waste, abuse or errors by the provider; a second program analytic may be configured to assessing whether behavior of the particular provider involved in the healthcare claim is consistent with a provider signature corresponding to that provider and generated based at least in part on historical data; a third program analytic may be configured for assessing interactions (e.g., shared patients) between a plurality of providers to determine whether any multi-provider behavior is indicative of fraud; and/or a fourth analytic may be configured for reconstructing a patient's historical medical record to determine whether a particular healthcare claim is expected based at least in part on the patient's history.

Various embodiments are directed to an analytic platform for processing a claims record. In certain embodiments, the analytic platform comprises one or more memory storage areas and one or more processors configured to: receive a record data file; compress the record data file to generate a common data input object comprising a plurality of data elements, wherein each of the plurality of data elements represents one or more attributes of the record data file; pass the common data input object as input to a plurality of analytics executing independently and in parallel, and wherein: each of the plurality of analytics retrieves at least one compressed parameter file for use in processing data elements of the common data input object; and each of the plurality of analytics is configured to generate respective outputs based at least in part on one or more of the plurality of data elements of the common data input object; and combine the respective outputs from each of the plurality of analytics into a common output object.

In certain embodiments, the one or more processors are further configured to: receive historical data files relating to an actor identified within at least one record data file; compress the one or more historical data files to generate a historical summary data file relating to the actor; and wherein the at least one compressed parameter file retrieved by at least one of the plurality of analytics is embodied as the historical summary data file relating to the actor.

In various embodiments, the plurality of analytics comprise one or more of: a fraud, waste, abuse, and error (FWAE) scoring analytic; a provider signature analytic; a provider network analytic; or a historical medical record analytic. Moreover, the plurality of analytics may comprise the FWAE scoring analytic, and wherein the FWAE scoring analytic may be configured to: parse the common data input object to identify one or more contexts relating to an underlying claim record; retrieve at least one compressed parameter file relating to each of the identified one or more contexts; and generate a respective output comprising a score value for the common data input object. In certain embodiments, the FWAE scoring analytic is further configured to generate a human-readable narrative corresponding to the score value. In various embodiments, the one or more contexts relating to the underlying claims record comprise one or more of: a patient identity, a provider identity, an entity identity, or a medical claim. Moreover, the at least one compressed parameter file may be generated periodically based at least in part on historical data relating to a respective context of the one or more contexts. In certain embodiments, the historical data is embodied as historical data generated during a moving time period having a defined length.

In various embodiments, the plurality of analytics comprises the provider signature analytic, and wherein the provider signature analytic may be configured to: parse the common data input object to identify a provider relating to an underlying claim record; retrieve a compressed parameter file comprising historical data relating to the provider; and generate a respective output identifying whether data elements within the common data input object are consistent with the compressed parameter file.

Various embodiments are directed to a method for processing a claims record. In certain embodiments, the method comprises: receiving a record data file; compressing the record data file to generate a common data input object comprising a plurality of data elements, wherein each of the plurality of data elements represents one or more attributes of the record data file; passing the common data input object as input to a plurality of analytics executing independently and in parallel, and wherein: each of the plurality of analytics retrieves at least one compressed parameter file for use in processing data elements of the common data input object; and each of the plurality of analytics is configured to generate respective outputs based at least in part on one or more of the plurality of data elements of the common data input object; and combining the respective outputs from each of the plurality of analytics into a common output object.

In certain embodiments, the method further comprises: receiving historical data files relating to an actor identified within at least one record data file; compressing the one or more historical data files to generate a historical summary data file relating to the actor; and wherein the at least one compressed parameter file retrieved by at least one of the plurality of analytics is embodied as the historical summary data file relating to the actor.

In various embodiments, the plurality of analytics comprise one or more of: a fraud, waste, abuse, and error (FWAE) scoring analytic; a provider signature analytic; a provider network analytic; or a historical medical record analytic. Moreover, in embodiments in which the plurality of analytics comprises the FWAE scoring analytic, and the FWAE scoring analytic may be configured to: parse the common data input object to identify one or more contexts relating to an underlying claim record; retrieve at least one compressed parameter file relating to each of the identified one or more contexts; and generate a respective output comprising a score value for the common data input object. Moreover, the one or more contexts relating to the underlying claims record may comprise one or more of: a patient identity, a provider identity, an entity identity, or a medical claim.

In certain embodiments, the plurality of analytics comprises the provider signature analytic, and wherein the provider signature analytic may be configured to: parse the common data input object to identify a provider relating to an underlying claim record; retrieve a compressed parameter file comprising historical data relating to the provider; and generate a respective output identifying whether data elements within the common data input object are consistent with the compressed parameter file.

Various embodiments are directed to a computer program product comprising a non-transitory computer readable medium having computer program instructions stored therein, the computer program instructions when executed by a processor, may be configured to cause the processor to: receive a record data file; compress the record data file to generate a common data input object comprising a plurality of data elements, wherein each of the plurality of data elements represents one or more attributes of the record data file; pass the common data input object as input to a plurality of analytics executing independently and in parallel, and wherein: each of the plurality of analytics retrieves at least one compressed parameter file for use in processing data elements of the common data input object; and each of the plurality of analytics is configured to generate respective outputs based at least in part on one or more of the plurality of data elements of the common data input object; and combine the respective outputs from each of the plurality of analytics into a combined common output object.

In certain embodiments, the computer program instructions when executed by a processor, cause the processor to: receive historical data files relating to an actor identified within at least one record data file; compress the one or more historical data files to generate a historical summary data file relating to the actor; and wherein the at least one compressed parameter file retrieved by at least one of the plurality of analytics is embodied as the historical summary data file relating to the actor. Moreover, the plurality of analytics may comprise one or more of: a fraud, waste, abuse, and error (FWAE) scoring analytic; a provider signature analytic; a provider network analytic; or a historical medical record analytic. In embodiments in which the plurality of analytics comprises the FWAE scoring analytic, the FWAE scoring analytic may be configured to: parse the common data input object to identify one or more contexts relating to an underlying claim record; retrieve at least one compressed parameter file relating to each of the identified one or more contexts; and generate a respective output comprising a score value for the common data input object.

In embodiments in which the plurality of analytics comprises the provider signature analytic, the provider signature analytic may be configured to: parse the common data input object to identify a provider relating to an underlying claim record; retrieve a compressed parameter file comprising historical data relating to the provider; and generate a respective output identifying whether data elements within the common data input object are consistent with the compressed parameter file.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

Figure 1:
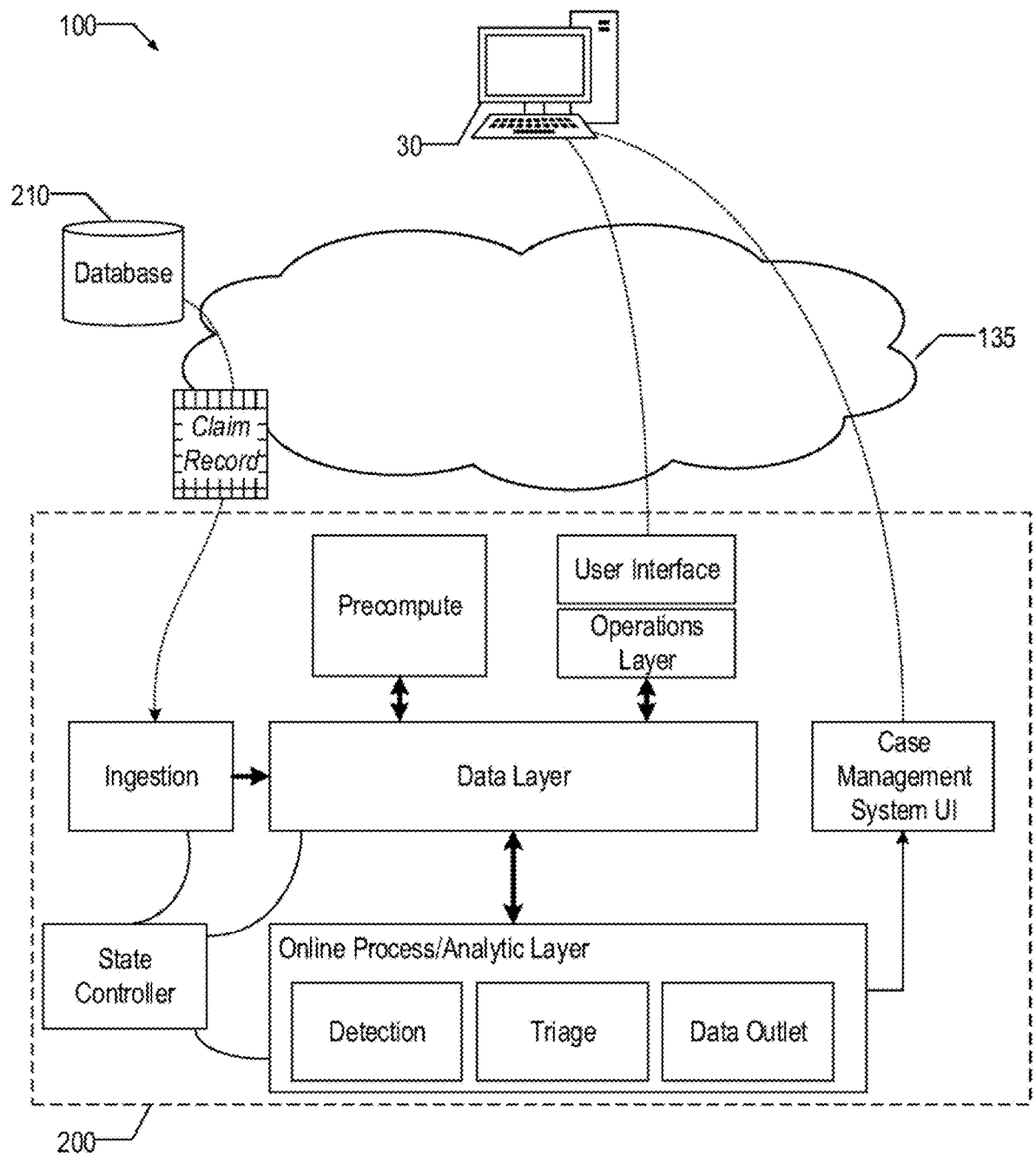
FIG. 1 shows a networked environment in which various embodiments operate.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

I. OVERVIEW

Various embodiments encompass systems and methods for processing vast amounts of medical claims data in real-time, as individual medical claims are presented for reimbursement from a provider by a payer to determine whether a particular medical claim is indicative of fraudulent behavior that warrants additional investigation prior to reimbursement. Due to the ever-changing nature of healthcare fraud, the described systems and methods are configured for reviewing several aspects of a particular medical claim within the context of known facts and/or behavioral trends of the provider, healthcare service location, and/or patient to provide a complete view of the claim when viewed by a claims examiner. Moreover, the system and method is configured for modular execution of various analytics utilized to analyze a particular claim, such that each analytic may be easily updated, or new analytics may be easily added while maintaining a low latency processing characteristic when reviewing each claim for possible fraud indicators.

Various embodiments employ parallel processing strategies for executing a plurality of program analytics in parallel and based at least in part on a common data input object to minimize the overall processing resources required to generate a complete, common output object relating to a single medical claim. The plurality of program analytics need not be executed simultaneously under the parallel processing strategy, but may instead be executed at different times (e.g., to conserve processing resources). To ensure a common data object may be easily consumed and utilized by each of the plurality of executing program analytics, the data object is embodied as a compressed and standardized data object generated based at least in part on healthcare "837 claims records," which are known to be characterized by a number of variables both in terms of the included content of the claims record, as well as the formatting of these claims records. The generated common data input object comprises data elements necessary as input for execution of each of the plurality of program analytics.

Those data analytics may be embodied as (1) a fraud, waste, abuse, and error (FWAE) scoring analytic; (2) a provider signature analytic; (3) a provider network analytic; and (4) a historical medical record analytic. However, as mentioned above, these analytics are presented in a modular fashion that may be easily substituted for other analytics, or new analytics may be easily added in addition to those discussed in detail herein.

Moreover, each of these program analytics may be configured to execute utilizing the common data input object as input (which may be utilized together with other data retrieved from other data sources, for example, providing data indicative of a particular provider's specialty), and at least a subset of the executing program analytics may be configured to utilize other compressed data features as parameters to be utilized when executing on a particular data object relating to a particular healthcare claim. For example, a provider signature analytic may be configured to execute utilizing compressed parameters indicative of a particular provider's recent historical behavior. The compressed parameters may be indicative of the number of claims typically submitted by the provider (and/or whether there has been a drastic change in the number of claims submitted by the provider), the type of claims typically submitted by the provider, the average cost of claims typically submitted by the provider, and/or the like. Such parameters may be compressed summary data of the provider's historical behavior, such that additional claims data involving the provider need not be separately reviewed. Additional detail regarding the execution of each program analytic is provided herein.

Ultimately, the program analytics are configured to output data to a common output object ultimately presented to a user (e.g., via a user interface). The common output object may be assembled and presented to the user via a display. Moreover, in certain embodiments, the common output object may comprise one or more interactive features configured to enable a user to access the original 837 claims data relating to a medical claim, and/or to access other data utilized by the one or more program analytics (e.g., when assembling compressed parameters for individual program analytics) upon a determination that further investigation into potential fraud is warranted for a particular claim.

a. Technical Problem to be Solved

Current medical claim fraud detection methodologies require a significant amount of human review and processing resources. Combining these two limitations means that the claim review process requires a significant amount of time, and must often be performed after a claim has been paid due at least in part to these timing limitations. Computing systems configured for processing medical claims to identify potential indicators of fraud are incapable of processing these claims quickly, at least in part due to the vast amount of data generated as a part of each claim, as well as the sheer volume of claims generated every second. Existing medical claims are often summarized using known "837 claims records" (e.g., presented in Electronic Data Interchange (EDI) X-12 format in which data may be organized into segments, wherein each segment contains multiple data elements) which include data indicative of various healthcare services performed as a part of a medical claim. These 837 claims records also include data indicative of the patient involved, the providers involved, a healthcare entity involved (e.g., a hospital, medical office, and/or the like), and/or the like. Given the sheer volume of relevant data within these 837 claims records, each 837 claims record may include approximately 12,000 data fields that must be processed. Moreover, healthcare payers have been known to receive millions of claims per day, thereby providing a huge amount of data that must be sorted and reviewed for potentially fraudulent claims. Reviewing each of these medical claims using the complete 837 claim records introduces a great deal of latency into the process of reviewing each medical claim, thereby rendering real-time processing of claims infeasible utilizing technologies currently in use.

b. Technical Solutions

To overcome the technical difficulties associated with processing massive data sets to identify potentially fraudulent behavior, without notable latency, various embodiments utilize compressed and standardized data objects as input for various fraud detection related program analytics. The common data input object, which may be generated based at least in part on a medical claims data record (e.g., an 837 claim record), comprises data elements necessary for execution of each of the program analytics, which may be configured to execute in parallel. This parallel program analytic execution strategy minimizes the collective execution time for the fraud detection program analytics, thereby further reducing latency associated with executing such a collection of programs.

Moreover, each of the plurality of program analytics may utilize compressed parameters, for example, summarizing characteristics of a particular actor involved in a particular claim. For example, compressed historical medical records may be constructed for a particular patient to determine whether services provided in a current claim are sufficiently related to the patient's historical claims. As another example, compressed data indicative of a provider's recent, typical practice (e.g., average number of claims submitted, average cost of claims submitted, and/or the like) may be generated and utilized by a corresponding program analytic to determine whether a particular claim (or a collection of claims) is out of the ordinary for the provider. This use of compressed parameter data within each program analytic further reduces latency associated with execution of the fraud detection system as a whole, thereby enabling the system to be executed prior to and/or concurrently with paying the medical claim.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program analytics, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like). A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combinations of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

FIG. 1 provides an illustration of data connections usable within an analytic platform 100 that can be used in conjunction with various embodiments of the present invention. As shown in FIG. 1, the data connections of an analytic platform 100 may comprise one or more computing entities 200, one or more user computing entities 30, one or more networks 135, one or more databases 210, and/or the like. Each of these entities may define one or more outward facing aspects, which may be interactive with other entities within the analytic platform 100. Specifically as indicated with respect to the one or more computing entities 200, one or more user interfaces (e.g., enabling users to view/retrieve generated output, and/or a separate case management system user interface) may be accessible via a user computing entity 30, and an ingestion portion may be accessible via a database 210 (e.g., to provide 837 claim records to the computing entity 200 for processing in accordance with various embodiments discussed herein). Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

a. Exemplary Computing Entity

Figure 2:
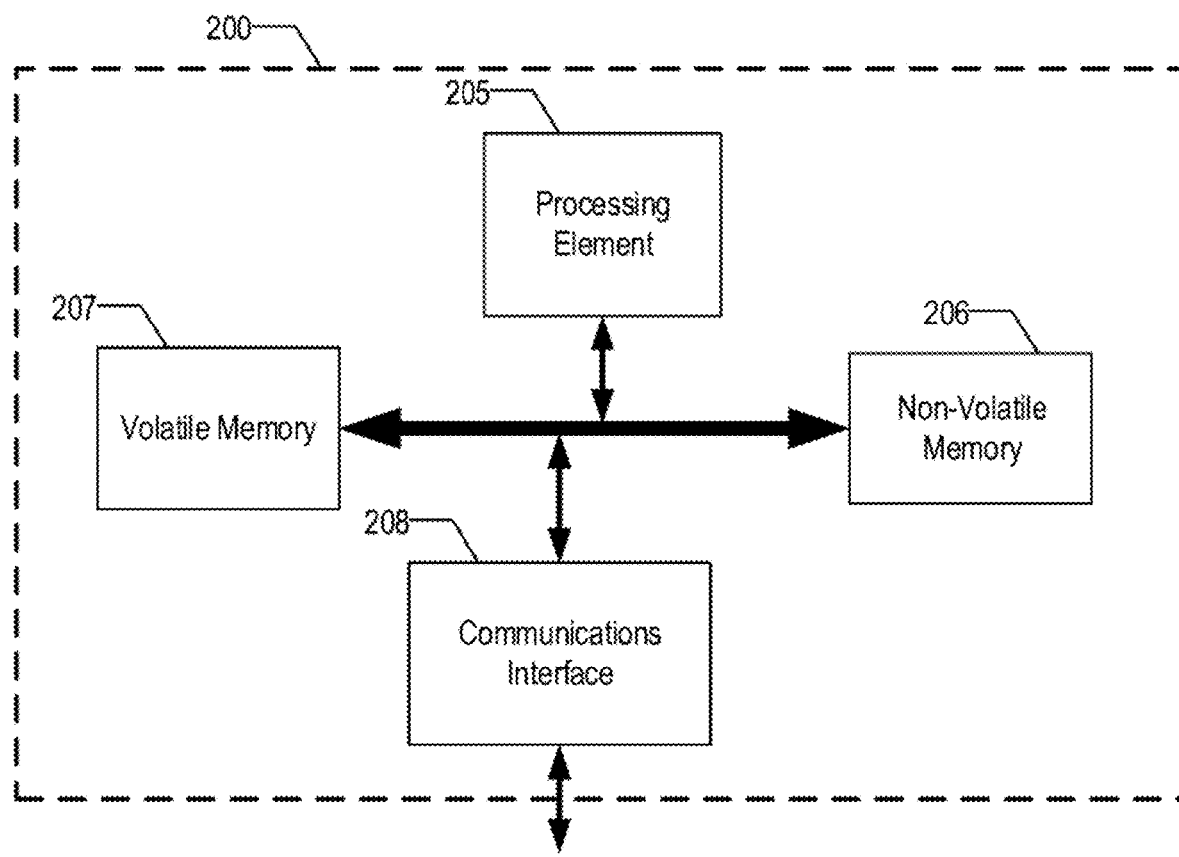
FIG. 2 shows a schematic of an example computing entity according to various embodiments.

FIG. 2 provides a schematic of a computing entity 200 according to one embodiment of the present invention. As discussed in greater detail herein, the various analytics may execute via a computing entity 200 similar to that described in reference to FIG. 2. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, clusters, blades, gateways, switches, processing devices, processing entities, set-top boxes, relays, routers, network access points, base stations, the like, and/or any combination of devices or entities adapted to perform the steps, functions, operations, and/or processes described herein. Such steps, functions, operations, and/or processes may include, for example, transmitting, receiving, operating on, processing, displaying, storing, determining, creating/generating, monitoring, evaluating, comparing, and/or similar terms used herein interchangeably. In one embodiment, these steps, functions, operations, and/or processes can be performed on data, content, information, and/or similar terms used herein interchangeably.

Such computing entities 200 may be embodied as one or more intake systems 402, one or more pre-generated parameter storage areas 403 (and/or associated processing systems), one or more analytic execution platforms 404, one or more systems 405, one or more raw data compilers, data parsers, and/or the like. As mentioned throughout this description, these components may be embodied as standalone computing devices, or one or more of these components may be integrated into a single computing device. Regardless of the number of individual computing devices utilized to perform the various processes discussed in reference to the each computing entity 200, the various components of each individual computing entity 200 may operate cohesively. These computing entities will be described in greater detail in reference to FIG. 4, below.

As indicated, in one embodiment, the computing entity 200 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the computing entity 200 may communicate with other computing entities 200, one or more user computing entities 30, and/or the like. Moreover, network and/or communications interfaces 208 may be configured for performing ingestion functionalities (e.g., ingesting an 837 claims record from a data source (e.g., database 210)), as indicated at FIG. 1.

As shown in FIG. 2, in one embodiment, the computing entity 200 may include or be in communication with one or more processing elements 205 (also referred to as processors, processing circuitry, and/or similar terms used herein interchangeably) that communicate with other elements within the computing entity 200 via a bus, for example. The processing elements 205 may perform a number of different functionalities, such as data layer functionalities, precompute functionalities, online processing functionalities (e.g., detection, triage, and data outlet generation functionalities), reporting layer functionalities, all of which are illustrated in FIG. 1. The processing elements 205 may further perform control functionalities, such as those of state controller as indicated in FIG. 1. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the computing entity 200 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program analytics, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

Memory media 206 may also be embodied as a data storage device or devices, as a separate data store server or servers, or as a combination of data storage devices and separate data store servers. For example, as shown in FIG. 1, the memory media 206 may be embodied as one or more databases 210 (e.g., an intake system 402 storage area, a pre-generated parameter storage area 403, a common output object 405 storage area, and/or the like). Further, in some embodiments, memory media 206 may be embodied as a distributed repository such that some of the stored data is stored centrally in a location within the system and other data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the data required for the operation of the analytic platform 100 may be stored. As a person of ordinary skill in the art would recognize, the data required for the operation of the analytic platform 100 may also be partially stored in the cloud data storage system and partially stored in a locally maintained data storage system.

In one embodiment, the computing entity 200 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program analytics, scripts, source code, object code, byte code, compiled code, interpreted code, machine code, executable instructions, and/or the like being executed by, for example, the processing element 305. Thus, the databases, database instances, database management system entities, data, applications, programs, program analytics, scripts, source code, object code, byte code, compiled code, interpreted code, machine code, executable instructions, and/or the like may be used to control certain aspects of the operation of the computing entity 200 with the assistance of the processing element 205 and operating system.

As indicated, in one embodiment, the computing entity 200 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the computing entity 200 may communicate with computing entities or communication interfaces of other computing entities 200, user computing entities 30, and/or the like.

As indicated, in one embodiment, the computing entity 200 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the computing entity 200 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The computing entity 200 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the computing entity's 200 components may be located remotely from other computing entity 200 components, such as in a distributed system. Furthermore, one or more of the components may be aggregated and additional components performing functions described herein may be included in the computing entity 200. Thus, the computing entity 200 can be adapted to accommodate a variety of needs and circumstances.

b. Exemplary User Computing Entity

Figure 3:
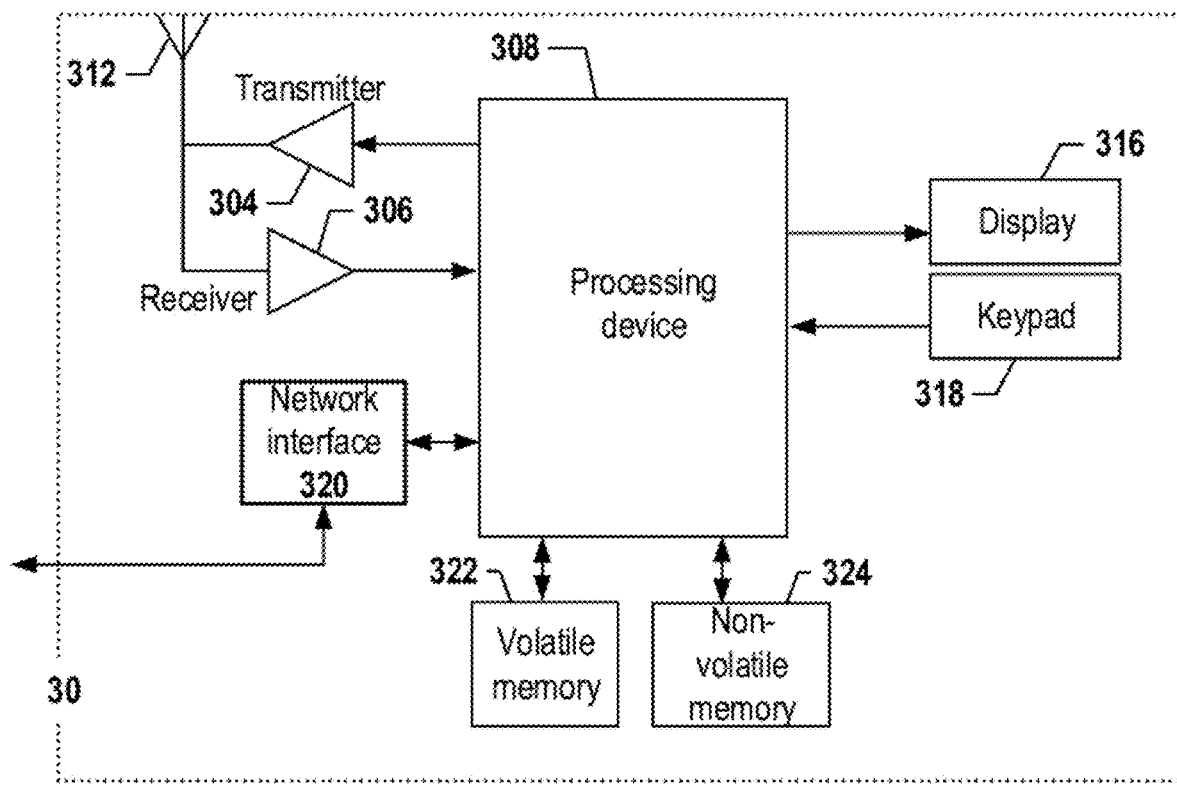
FIG. 3 shows an example user computing entity according to various embodiments.

FIG. 3 provides an illustrative schematic representative of user computing entity 30 that can be used in conjunction with embodiments of the present invention. The user computing entity 30 may be usable by any of a variety of "users," which may encompass one or more individuals, companies, organizations, entities, departments within an organization, representatives of an organization and/or person, and/or the like. These users may have various roles, such as administrative users controlling access to various aspects of the analytic platform 100 and/or controlling the integration of various features of the analytic platform 100, developers associated with user-generated program analytics (e.g., providing program analytics that may be incorporated as new modules of an overall system of analytics), end-users seeking the data output from a previously generated workflow, and/or the like.

As shown in FIG. 3, a user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a computing entity 200, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing device 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program analytics), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the computing entity's 200 position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface device comprising one or more user input/output interfaces (e.g., a display 316 and/or speaker/speaker driver coupled to a processing element 308 and a touch presentation, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as presentation savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program analytics, scripts, source code, object code, byte code, compiled code, interpreted code, machine code, executable instructions, and/or the like to implement the functions of the user computing entity 30.

c. Exemplary Networks

In one embodiment, any two or more of the illustrative components of the architecture of FIG. 1 may be configured to communicate with one another via respective communicative couplings to one or more networks 135. The networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

IV. EXEMPLARY SYSTEM OPERATION

Figure 4:
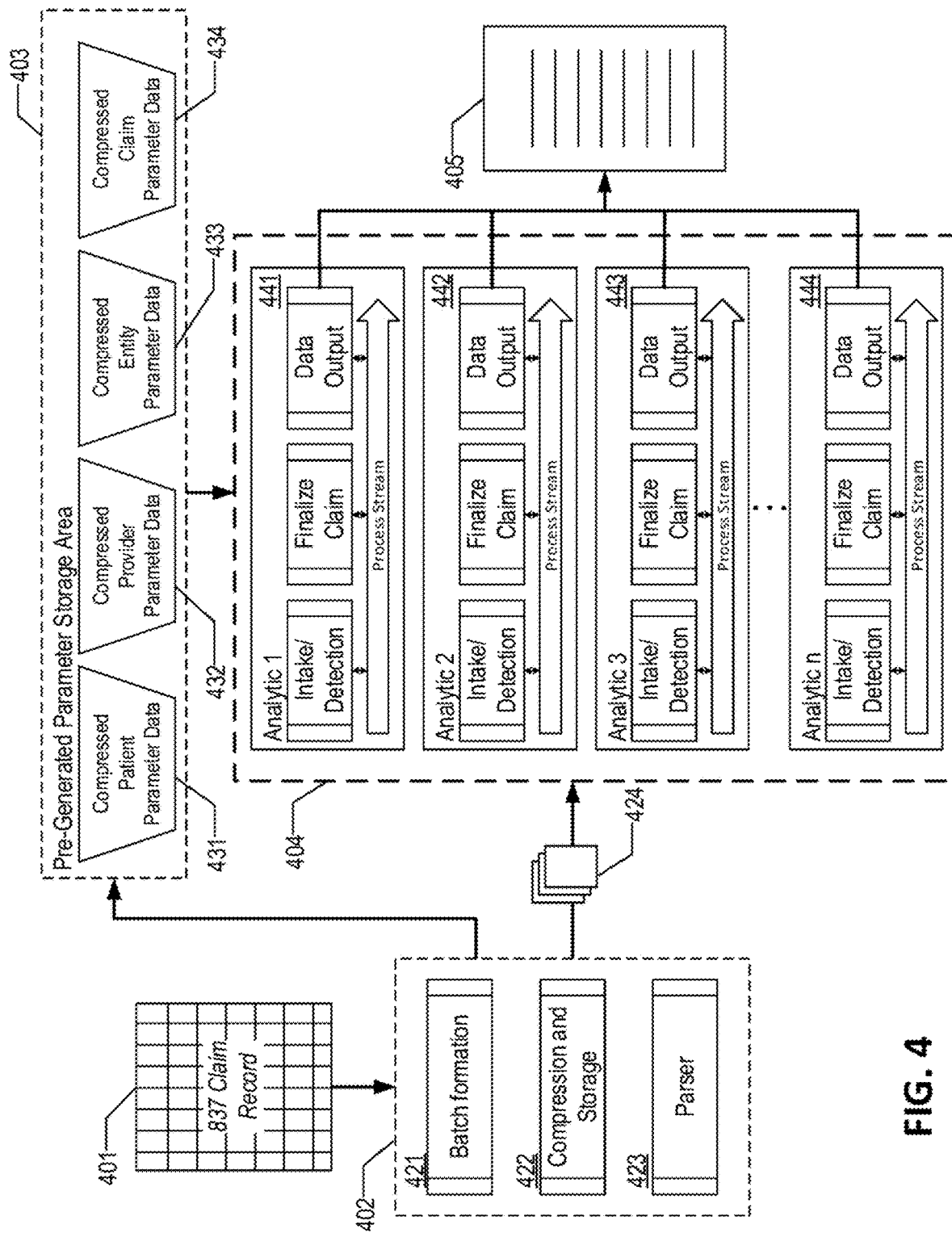
FIG. 4 schematically illustrates data flow paths according to various embodiments.

Example data flows will now be described with reference to FIGS. 4-12. As discussed therein, FIG. 4 provides a schematic view of data flow within the analytic platform 100, and each of FIGS. 5-12 provide additional illustrations relating to the particular functionality of various example analytics according to various embodiments. While the illustrated examples are specifically focused on the functionality of various configurations in processing healthcare-related data, it should be understood that various embodiments may be utilized in any of a variety of industries for processing large amounts of data in an efficient manner characterized by low levels of latency. As other examples, various embodiments may be configured for executing parallel analytics relevant to commercial-sales related data; web-crawling and/or search related data; and/or the like.

As discussed herein, the analytic platform 100 is configured to execute a plurality of program analytics (e.g., analytics 1-n 441, 442, 443, 444 as shown in FIG. 4) each configured to generate a particular portion of a data output. Moreover, each program analytic 441-444 is configured to utilize a particular data input generated (e.g., by input system 402 based at least in part on healthcare claims data generated in accordance with industry-known "837 claims records" 401). However, because these 837 claims records 401 contain large quantities of superfluous data, and because the format of data presented within the 837 claims records 401 is not standardized, the analytic platform 100 is configured to compress the data included within each 837 claims record 401 into a common data input object 424 having a fixed size and format, and including necessary data elements to be utilized by each of the program analytics to be executed by the analytic platform 100 (it should be understood that each individual analytic need not utilize every data element included within the common data input object 424). The intake system 402 of the analytic system 100 is thus configured to intake 837 data records 401, and to utilize an incorporated compression and storage subsystem 422 to generate the common data input objects 424. Moreover, the intake system 401 may additionally comprise a batch formation subsystem 421 configured for temporarily storing various common data input objects 424 for transmission as a batch to a pre-generated parameter storage area 403 and/or an analytic system 404. In certain embodiments, the intake system 402 may additionally comprise a parser subsystem 423 configured for parsing portions of received 837 data records to identify particular data elements stored therein, and a portion of those individual data elements may be included within the common data input object 424.

Thereafter, the analytic platform 100 is configured to execute a plurality of program analytics 441-444 (e.g., via analytic system 402) utilizing the common data input object as input for each of the program analytics 441-444. These program analytics 441-444 may comprise, for example, (1) a FWAE scoring analytic; (2) a provider signature analytic; (3) a provider network analytic; and/or (4) a historical medical claims analytic (e.g., which may encompass the concepts discussed in co-pending U.S. application Ser. No. 14/713,711, the contents of which are incorporated herein by reference in their entirety).

Each of these program analytics 441-444 may provide outputs to be stored within a generated data common output object 405 that may be presented to a user. In certain embodiments, each of the program analytics 441-444 provides an output that is indicative of a different angle that may be utilized to determine whether the underlying healthcare claim (that was the origin of the 837 claim record 401) is fraudulent.

a. Data Layer Functionality

The data layer functionality may encompass and/or otherwise relate to various processes for transforming ingested data into a format consumable by the various analytics. For example, 837 claims records 401 ingested via various embodiments are utilized to generate common data input objects 424 that may be utilized during processing described in reference to the analytic layer.

1. Generating a Common Data Input Object

As noted above, the program analytics 441-444 are configured for inputting a common data input object 424 comprising data elements indicative of various attributes of a medical claim. Thus, prior to executing any program analytics 441-444 for a particular medical claim, the analytic platform 100 is configured to generate a common data input object for each claim to be processed. In certain embodiments, an intake system 402 of the analytic platform 100 is configured to compress an 837 claim record 401 utilizing a lossy compression algorithm to generate a common data input object 424 having a significantly reduced object size relative to the 837 claim record 401. Moreover, whereas the 837 claim record 401 may vary both in terms of content and format (e.g., the content and formatting of an 837 claim record 401 may vary based at least in part on the number of procedures involved in a particular medical claim), the common data input object 424 may have a fixed size and shape configured for encompassing varying amounts of data therein.

Figure 5:
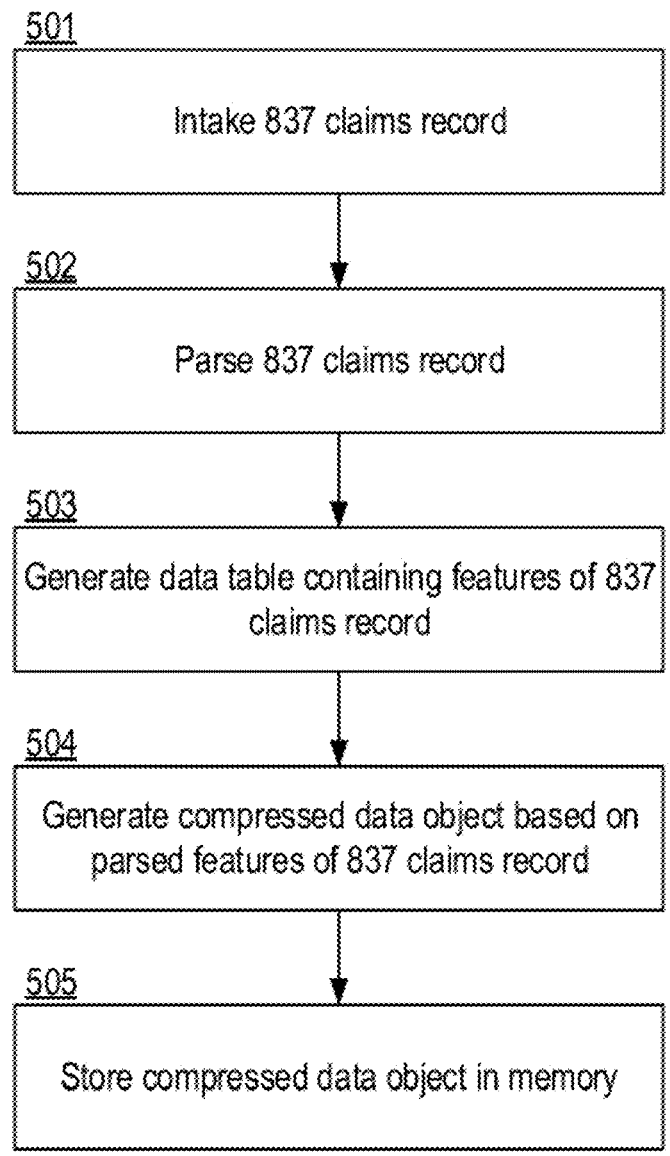
FIG. 5 illustrates a flowchart providing steps for generating a common input object according to various embodiments.

As illustrated in the flowchart of FIG. 5, which illustrates various steps performed in generating a common data input object, the intake system 402 is configured to intake an 837 claims record 401 for compression, as indicated at Block 501. Specifically, the intake system 402 may be configured to intake a plurality of 837 claims records 401 simultaneously and to generate a plurality of common data input objects 424 for later analysis. Thus, the intake system 402 may be configured for batch execution of compression processes, for example, during periods of time during which low levels of processing resources are utilized. It should be understood that other embodiments are configured for real-time processing of 837 claims records 401, such that each 837 claims record 401 is compressed when received.

In certain embodiments, the compression and storage subsystem 424 of the intake system 402 is configured to compress the data within the 837 claim record 401 into a common data input object 424 (e.g., which may compress the total included amount of data from several thousand data fields to several hundred data fields). Data fields/columns included within the common data input object 424 may be selected and/or generated based at least in part on data utilized as input for each of the program analytics 441-444 to be executed by the analytic platform 100. Thus, as program analytics 441-444 are added and/or modified, the fields included within the common data input object 424 may be updated to reflect the needed input for each of the program analytics 441-444. In certain embodiments, the fields included within the common data input object 424 may be adjusted manually, or automatically. For example, fields to be included within the common data input object 424 may be updated automatically by the analytic platform 100 based at least in part on data indicative of inputs required by each of the program analytics 441-444 to be executed.

As mentioned, the common data input object 424 has a defined format and/or shape in certain embodiments. However, the common data input object 424 may be configured to include data indicative of a variable number of procedures, codes, and/or the like. Thus, a single common data input object 424 may be configured to include data elements representing all procedures and/or other attributes of a single comprehensive medical claim. In certain embodiments, the common data input object 424 may thus comprise a plurality of data fields that may be selectably populated with substantive data elements or populated with null data elements. In other words, certain of the data fields within the common data input object may be configured to operate as placeholders in the event that a particular medical claim does not require all of the included data fields to provide complete information about a particular medical claim.

In certain embodiments, the common data input objects 424 may be generated in real time, as medical claims are received at the analytic platform 100.

Once a particular data record corresponding to a particular medical claim (e.g., an 837 claim record 401) is received, the analytic platform 100 executes a parser 423 on the received data record to parse the 837 claim record (as indicated at Block 502) to identify various raw data elements stored therein. In certain embodiments, a subset of those raw features may be compressed or otherwise selected for inclusion within the common data input object 424. As mentioned above, the 837 claims records 401 may each contain several thousand data elements, each of which may be represented by a corresponding one raw feature. The parser 423 may generate a data table comprising fields containing raw data elements parsed from the data record, as indicated at Block 503. In the healthcare context, these data fields may comprise data indicative of procedure codes associated with the medical claim, modifiers utilized during the medical claim, and/or the like.

Upon generation of the data table, the analytic platform 100 is configured to compress the data table into the common data input object 424 (e.g., via the compression and storage subsystem 422 of the intake system 402), as indicated at Block 504. In certain embodiments, data to be included within the common data input object 424 is selected based at least in part on feature engineering processes during which particular components of various analytics are identified, such that the common data input object 424 contains necessary data elements for execution of those analytics. The common data input object 424 may be stored (e.g., in a memory) temporarily until the program analytics 441-444 intake the common data input object 424 for execution, as indicated at Block 505.

In certain embodiments, the original 837 claim record 401 may be stored in a memory storage area for later reference. The 837 claim record 401 may be stored in a database in association with the common data input object generated therefrom, however the 837 claim record 401 may not be called as input for any program analytics 441-444. Instead, the 837 claim record 401 may remain available for access in the event that a user later determines that the 837 claim record 401 should be reviewed in closer detail (e.g., manually reviewed) to determine the likelihood of fraud relating to the particular medical claim.

b. Analytic Layer

Results of the data layer processing are then utilized within the analytic layer processing, which may be embodied by a plurality of parallel-executing program analytics. Each of those program analytics may be configured for generating a specific portion of an output data object that may be utilized within operations layer processing (which may, in certain embodiments, rely on user input provided based at least in part on the output data object).

1. Fraud, Waste, Abuse, and Error (FWAE) Scoring Analytic

One example of a program analytic that may be executed to highlight possible fraudulent behavior with respect to a particular medical claim is a FWAE scoring analytic configured to determine a comprehensive, single value score indicative of the likelihood that a particular medical claim is associated with fraudulent behavior. As shown in the schematic illustration of program analytics 441-444 of FIG. 4, and in the illustration of FIG. 6, the FWAE scoring analytic may comprise one or more subsystems operating in accordance with a process stream. Those subsystems may comprise an intake/detection subsystem for intaking input (e.g., the common data input object 424), extracting appropriate pre-compressed parameters for analyzing the input (e.g., from the pre-generated parameter storage area 403), and detecting whether the common data input object 424 is indicative of the presence of fraud. The subsystems may further comprise a subsystem for finalizing data relating to the claim (e.g., finalizing output data by assembling an output), and a subsystem for outputting the data for ultimate inclusion within an common output object 405.

The FWAE scoring analytic may be configured to review data stored within a common data input object 424 relative to a plurality of claim features. These claim features may be identified as reviewing (1) characteristics of a claim (e.g., the associated physician type, zip code where the procedure was performed, procedure type, and/or the like); (2) fraud detection characteristics (e.g., change in the number of claims submitted by a particular provider); (3) health claim characteristics (e.g., indicative of potential upcoding of procedures by a provider to more expensive claim types, unbundling of particular procedures into a plurality of claims, and/or the like); and/or the like. A framework for analyzing the claim in relation to these claim features may be stored within the analytic system 404 in association with the FWAE program analytic itself, and parameter data to be populated within the framework for particular claim comparisons may be retrieved from the pre-generated parameter storage area 403 based at least in part on data specific to a particular common data input object 424.

Because the FWAE scoring analytic is configured to summarize a plurality of practice features that may be indicative of the presence of fraud, the FWAE scoring analytic may be associated with one or more underlying processing systems generated in accordance with feature engineering processes for generating appropriate features to be considered by the FWAE scoring analytic. In certain embodiments, those feature engineering processes may be configured to generate appropriate outputs that may be indicative of various types of fraud, waste, abuse, and/or errors that may embodied within a particular provider's practice. Moreover, the feature engineering processes may be configured to identify appropriate methodologies for generating those outputs (e.g., embodied as model segmentation algorithms that may be executed via processing entities), and/or for identifying necessary inputs for generating those outputs (those inputs being particular features that may be included within a common data input object 424 and which may be generated based at least in part on raw data included within the 837 claim records 401), as reflected in FIG. 6. Those processing systems may be configured for populating the framework associated with the FWAE scoring analytic as mentioned above. One or more of the features to be considered by the FWAE scoring analytic may be generated manually (e.g., by an administrative user) or automatically (e.g., by the analytic platform 100). In those embodiments in which the analytic platform 100 is configured to automatically generate one or more features, the analytic platform 100 may be configured to utilize machine learning algorithms, artificial intelligence algorithms, and/or the like to generate such features. The analytic platform 100 may utilize prior data (e.g., historical data indicative of claims known to be fraudulent) to train appropriate machine learning and/or artificial intelligence models to identify appropriate features for use by the FWAE scoring analytic.

These features may be identifiable data elements extracted from the common data input object (e.g., data indicative of the age of a patient associated with a claims record utilized to generate the common data input object 424), characteristics of identifiable relationships between various data elements extracted from the common data input object 424 (e.g., a relationship between the age of a patient and the procedure performed on that patient), and/or the like.

Figure 6:
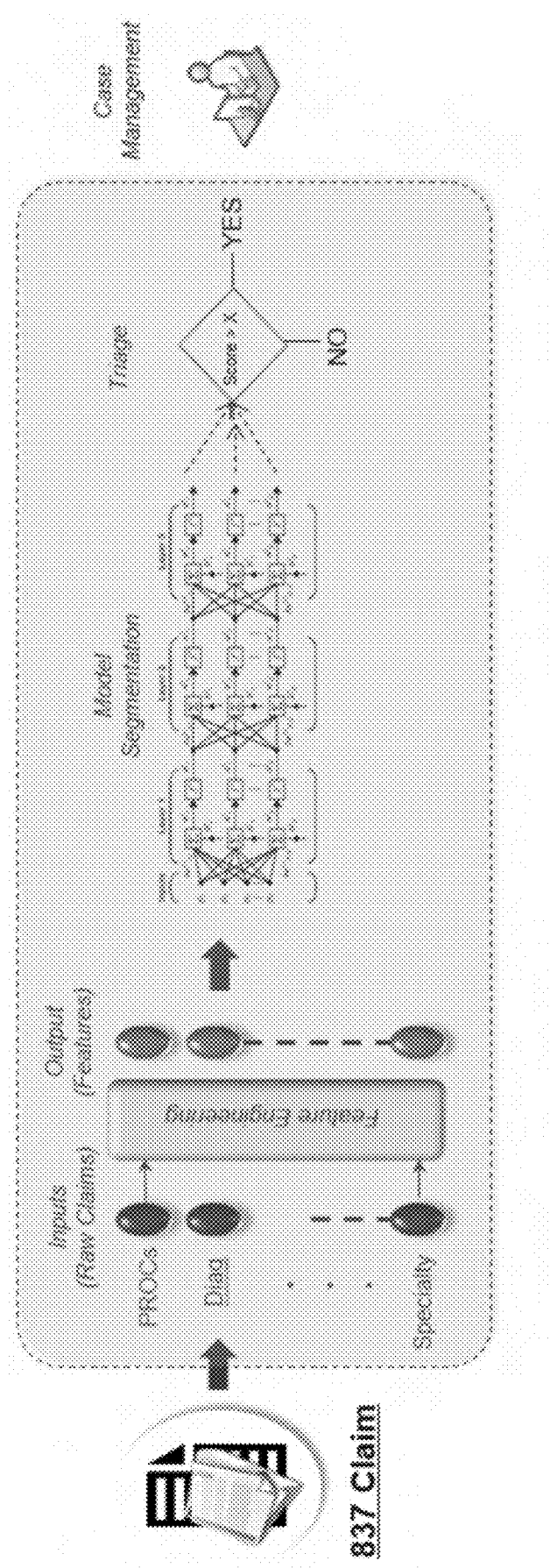
FIG. 6 graphically illustrates various steps performed b y a fraud, abuse, waste, and error scoring analytic.

As indicated in FIG. 6, the generated features are represented within one or more models (e.g., a predictive model) utilized by the FWAE scoring analytic to generate a score for a particular medical claims record. In use, a common data input object 424 is input into the scoring analytic which encompasses a scoring algorithm encompassing the features. Based at least in part on the features within the scoring algorithm, the FWAE scoring analytic generates a summary score indicative of the likelihood that a particular claim encompasses fraudulent activity.

Figure 7:
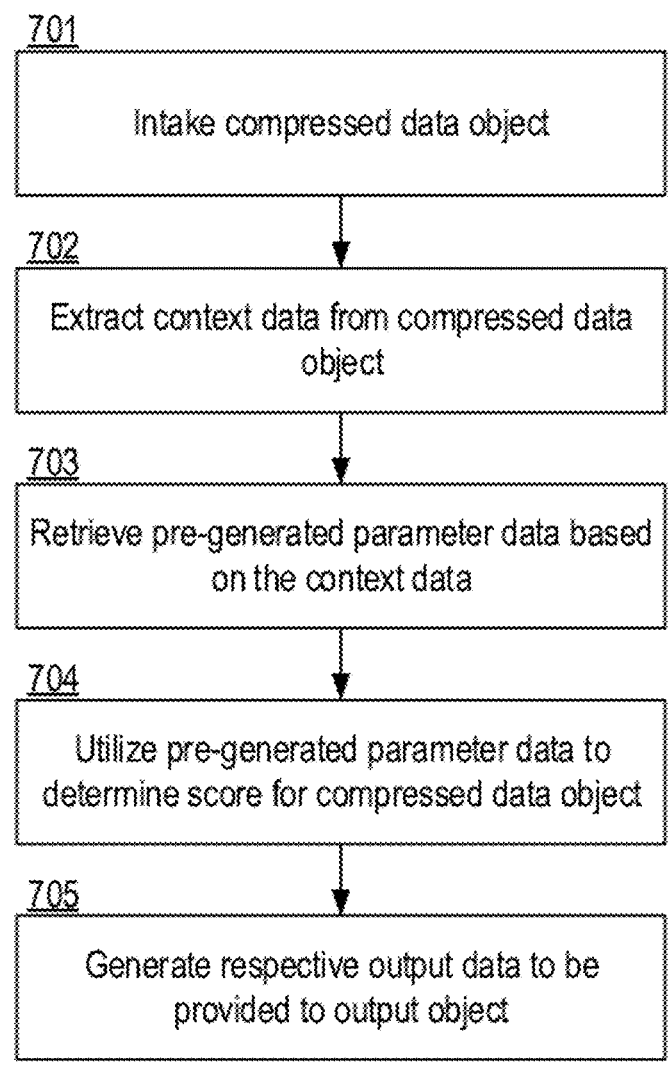
FIG. 7 illustrates a flowchart providing steps executed by a fraud, abuse, waste, and error scoring analytic.

To provide a complete view of the processes involved in executing the FWAE scoring analytic, FIG. 7 is an illustrative flowchart showing various steps performed by the FWAE scoring analytic. As shown in FIG. 7, the analytic platform 100 is configured to provide the common data input object 424 (corresponding to a particular medical claim) to the FWAE scoring analytic as indicated at Block 701. The FWAE scoring analytic is then configured to parse the common data input object to identify one or more contexts associated with the underlying medical claim as indicated at Block 702. In certain embodiments, these contexts may comprise data indicative of (1) the patient/member; (2) the provider; (3) the entity associated with the provider (e.g., a hospital, office, and/or the like, which may be identified by a tax identifier); and/or (4) the claim itself. In certain embodiments, all data elements from the common data input object may be assigned to one or more of the contexts. In other embodiments, only a portion of the data elements included within the common data input object are assigned to one or more of the above-mentioned contexts.

The data retrieved from the common data input object and related to each of the above-mentioned contexts may operate as data retrieval keys. The FWAE scoring analytic may utilize these data retrieval keys to retrieve related historical data from the pre-generated parameter storage area 403 accessible via the analytic platform 100, as indicated at Block 703. For example, the FWAE scoring analytic may retrieve historical data relevant for the patient (e.g., compressed patient parameter data 431); historical data relevant for the provider (e.g., compressed provider parameter data 432); historical data relevant for the associated entity (e.g., compressed entity parameter data 433); historical data relevant for a particular claim type (e.g., compressed claim parameter data 434, which may encompass data indicative of typical circumstances surrounding a particular medical claim type, such as timing between claims, symptoms associated with the claim, a patient's typical age, and/or the like). Moreover, the historical data relevant to the various actors involved in the claim (e.g., the patient, provider, and/or entity) may be indicative of any historical involvement in fraud and/or may be indicative of various characteristics of those actors. Data indicative of whether a particular actor has been involved in fraud may be retrieved manually and provided to the analytic platform 100 for inclusion within the pre-generated parameter storage area 403, or the data indicative of whether a particular actor has been involved in fraud may be retrieved automatically, for example by a web crawler searching for publicly available data indicative of whether a particular actor has been involved in fraud. The web crawler may be configured to automatically provide such data to the pre-generated parameter storage area 403.

As mentioned, the historical data corresponding to the various contexts of the claims comprises compressed historical data generated periodically, for example, following a batch process (e.g., which may be performed by the batch formation subsystem 421 of the intake system 402). Because complete historical data relevant to a particular actor, even if the historical data encompasses data generated during a relatively short time period, generally comprises a relatively large amount of data, utilizing compressed summary data associated with each actor minimizes latency associated with retrieving appropriate historical data for those actors. Moreover, by generating/updating the compressed summary data periodically (e.g., weekly, every 3 days, every 10 days, and/or the like), the analytic platform 100 may be configured to utilize computing resources to generate/update the compressed summary data during periods of time having low processing resource demands.

In certain embodiments, the compressed historical data for each of the actors may be embodied as actor profiles (e.g., encompassing patient profiles, provider profiles, entity profiles, and/or the like). These profiles may encompass a moving historical summary of characteristics of the particular actor, over a most-recent set period of time. As a non-limiting example, the profiles may encompass data reflecting a summary of characteristics of a particular entity over the most recent 10-weeks, most recent 13-weeks, most recent 6-months, and/or the like. In embodiments in which these summaries are updated weekly, each update may remove the oldest reflected data, to be replaced by recent data for the particular entity. Moreover, these profiles may remain stagnant between updates. Referencing the non-limiting example of a weekly-update configuration, the actor profiles may remain fixed during use throughout a week, even though additional data may be generated for each actor during the week. The actor profiles may then be updated weekly (e.g., at the end of the week) to reflect the data generated during the prior week.

In certain embodiments, these compressed historical profiles retrieved for each actor associated with a particular claim may be compressed utilizing lossy compression algorithms, thereby resulting in relatively small data objects that may be retrieved and reviewed during execution of the FWAE scoring analytic. For example, the compressed historical profiles may comprise one or more summary scores, summary characteristics, and/or the like for a particular actor (e.g., patient, provider, entity, and/or the like), that may be compared against data elements retrieved from the common data input object during execution of an algorithm associated with the FWAE scoring analytic.

With reference again to the underlying process of executing the FWAE scoring analytic, the FWAE scoring analytic intakes the various historical data (e.g., actor profiles) retrieved based at least in part on the keys identified within the common data input object. Utilizing a scoring algorithm encompassing the various generated features discussed above, the FWAE scoring analytic generates an output (which may be embodied as an interim output ultimately included within an output data object as discussed herein) comprising a summary score indicative of the likelihood of fraud associated with the underlying claim, as indicated at Block 704. Ultimately, the output of the FWAE scoring analytic is stored as a part of the data common output object 405, discussed in greater detail herein. The output of the FWAE scoring analytic may comprise a plurality of data fields encompassing (1) a generated score, (2) one or more reason codes providing a textual description of the generated score, (3) textual descriptions of any factors deemed to have the largest influence (e.g., the top four factors that influenced the score) on the score, and/or the like. These factors deemed to have an influence on the generated score may comprise sets of individual features, with all of the features included within an individual set of features being relating to the same general pattern (e.g., a claim billing amount, a claim diagnosis code, a claim's procedures, the presence of potential up-coding, overuse of some procedure codes, and/or the like). The textual descriptions may comprise multiple sub-portions—a first subportion splits the identified most influential factors into their most important individual features, and a second subportion provides a description of the various contexts in which the current claim is evaluated (e.g., by evaluating the information in the claim itself, and/or by evaluating the information in the claim relative to historical data relating to an involved patient, provider, and/or billing entity). Moreover, the scoring analytic may be configured to generate a plain language explanation/narrative of the reasons underlying the score. The plain language explanation may be generated based at least in part on a plurality of pre-constructed explanatory phrases identified as relevant by the FWAE scoring analytic based at least in part on one or more of the features considered as a part of execution of the FWAE scoring analytic. As a non-limiting example, the FWAE scoring analytic may output a score indicating that an underlying claim has a high likelihood of being associated with fraudulent behavior. The FWAE scoring analytic may further output a narrative indicating that the score is relatively high because the provider involved in the claim has been known to be involved in medical claims fraud in the past, and the dollar amount of the claim is relatively high. These factors are mere examples, and the FWAE scoring analytic may be configured provide summary narratives regarding any of a variety of features that may be reflective of a particular score.

Moreover, as mentioned above, the FWAE scoring analytic may be one of a plurality of analytics that provide data output to a common output object ultimately presented to a user. Thus, the FWAE scoring analytic may pass the generated output (e.g., a score and/or a narrative associated with a particular score) to a memory storage area utilized to combine data elements to be presented as a part of a combined common output object to be presented to the user, as reflected at Block 705 of FIG. 7.

2. Provider Signature Analytic

In certain embodiments, the analytic platform 100 is configured to execute a provider signature analytic configured to determine whether the provider's behavior with respect to a particular claim represents a departure from the provider's typical practice behavior. In certain embodiments, the provider signature analytic may be configured to execute in parallel with the FWAE scoring analytic (and/or any other analytics described herein or otherwise executed by the analytic platform 100).

Like the FWAE scoring analytic discussed above, the provider signature analytic is configured to utilize the common data input object generated by the analytic platform 100 as input thereto. As shown in the schematic illustration of program analytics 441-444 of FIG. 4, the provider signature analytic may also comprise one or more subsystems operating in accordance with a process stream. Those subsystems may comprise an intake/detection subsystem for intaking input (e.g., the common data input object 424), extracting appropriate pre-compressed parameters for analyzing the input (e.g., from the pre-generated parameter storage area 403), and detecting whether the common data input object 424 is indicative of the presence of fraud. The subsystems may further comprise a subsystem for finalizing data relating to the claim (e.g., finalizing output data by assembling an output), and a subsystem for outputting the data for ultimate inclusion within a common output object 405.

Figure 9A:
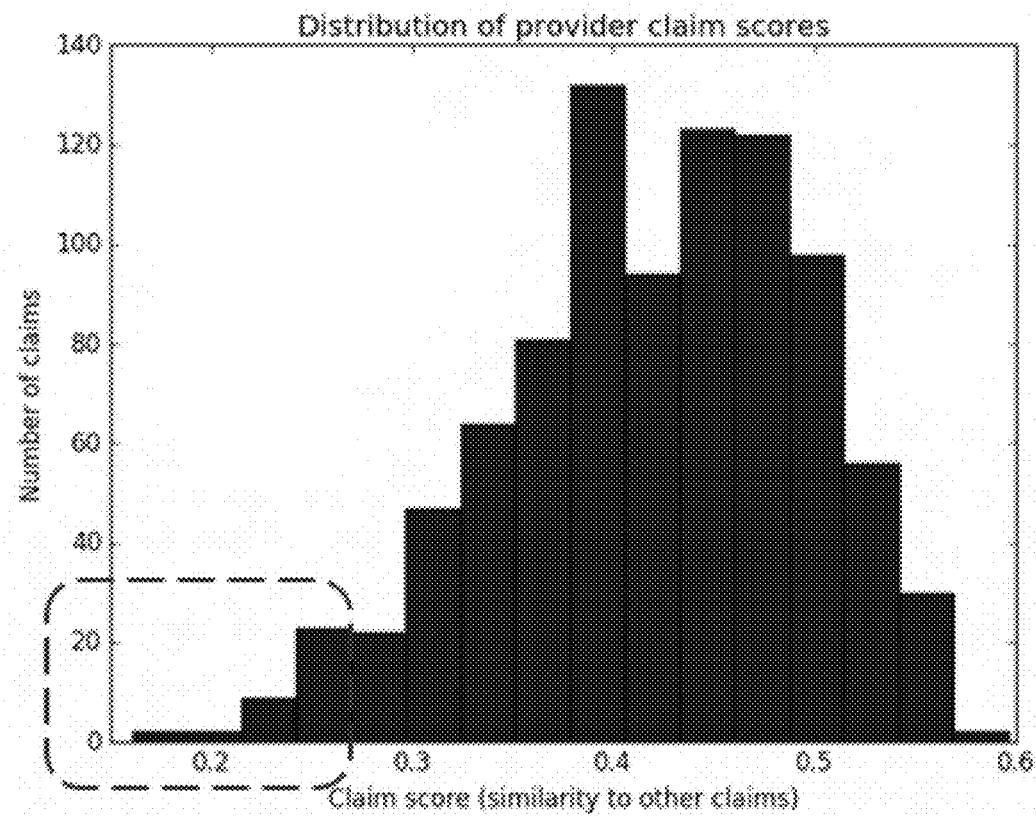
FIGS. 9A-9B illustrate example provider signature data utilized by a provider signature analytic.
Figure 9B:
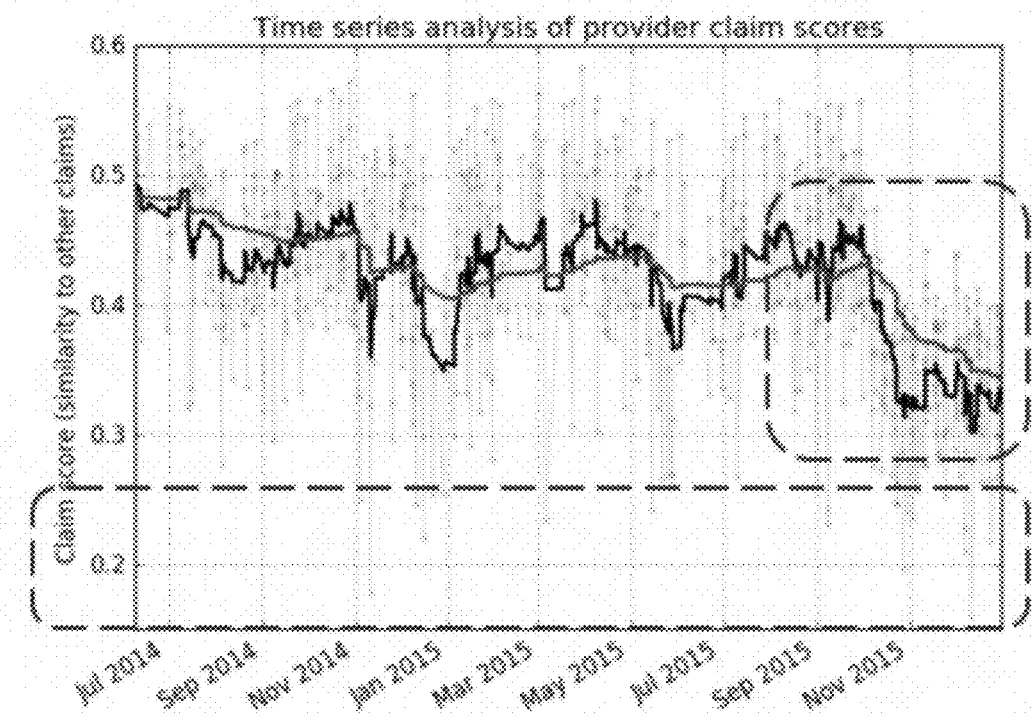

Moreover, the provider signature analytic may be configured to retrieve additional compressed data during the execution of various algorithms associated with the provider signature analytic. For example, the provider signature analytic may be configured to retrieve signature data associated with a provider involved with a particular claim (e.g., from a memory storage area). Graphically depicted examples of provider signature data is illustrated in FIGS. 9A-9B. Specifically, FIG. 9A illustrates data summarizing behavior of a plurality of providers, which may be utilized to determine whether a particular provider's behavior could be considered an outlier relative to other providers. FIG. 9B provides a provider-specific view of data, which may be utilized to determine trends within a provider's general practice, and/or to identify sudden changes in the provider's behavior, which may be indicative of the start of fraudulent behavior.

In certain embodiments, the provider may be identified by identifying context data within the common data input object 424 indicative of the provider associated with the claim (in a manner similar to that discussed above in reference to the FWAE scoring analytic). Moreover, the provider signature may be stored as a portion of, or in addition to the provider profile discussed above in reference to the FWAE scoring analytic. In certain embodiments, both the provider signature analytic and the FWAE scoring analytic may utilize the provider profile as parameters of algorithms executed as a portion of the respective analytics.

In certain embodiments, the provider signature may provide data indicative of historical behavior of a particular provider. The historical behavior represented within the provider signature may be limited to a particular time period, or the historical behavior may encompass a provider's entire career. Thus, the provider signature is representative of trends in the provider's behavior over time. For example, the provider signature may be representative of data indicative of the average number of claims submitted per week, the average cost of claims submitted per week, the typical types of claims submitted each week, and/or the like. The historical behavior of a particular provider may be utilized to determine one or more deviations against particular claims (e.g., a particular claim being evaluated for potential fraud). For example, specific portions of claim (e.g., a billed amount, procedure codes, member age, and/or the like) may be compared against historical data for the provider to determine an amount of deviation between the data within the claim and the historical data (e.g., the historical summary data). A deviation may be identified as the difference between the value for a particular portion of a claim and relevant historical data. As a specific example, a deviation for a billed amount may be the difference between the billed amount for a particular claim and the average billed amount for the provider. Deviations may be determined for a plurality of portions of a claim, and each deviation may be assigned a deviation score. The plurality of deviation scores generated for a particular claim may be combined to determine an overall deviation score for a particular claim. This overall deviation score may be compared against past deviation scores for the provider to determine whether the particular claim is consistent with the provider's prior history. Again, because the provider signature data may be presented as compressed data, the provider signature need not encompass all of the historical data records associated with the provider, but may instead encompass various summary data elements that may be usable by the provider signature analytic to determine whether a particular claim is likely indicative of the presence of fraud.

Figure 8:
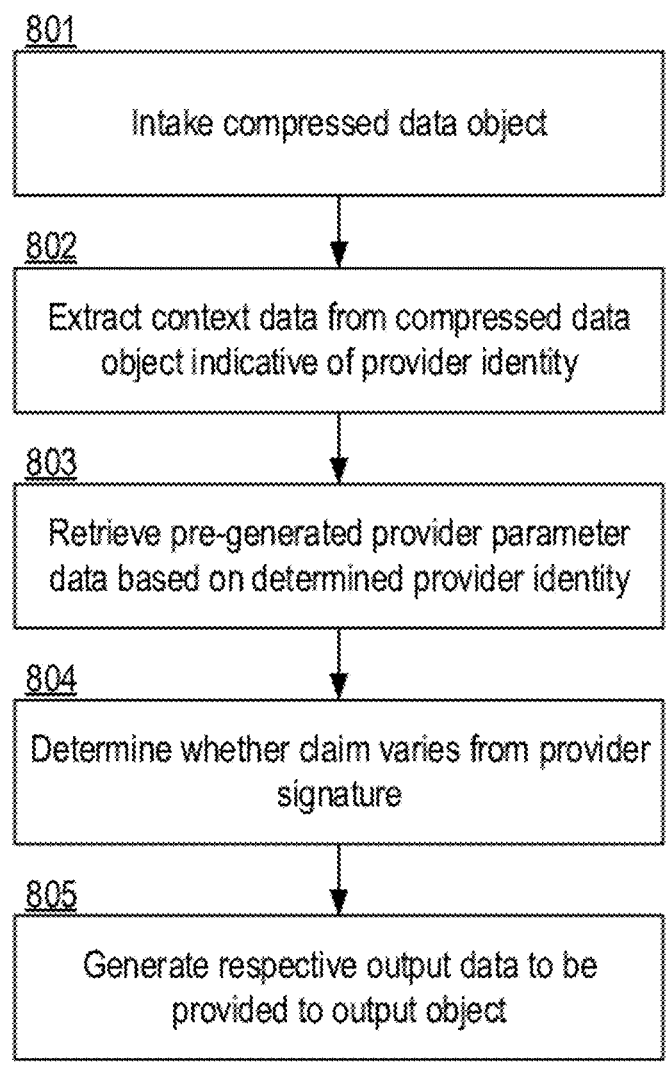
FIG. 8 illustrates a flowchart providing steps executed by a provider signature analytic.

FIG. 8 provides a flowchart illustrating a summary of operation of the provider signature analytic, the analytic platform 100 provides the common data input object to the provider signature analytic for execution. Upon receipt of the common data input object 424 (as indicated at Block 801), the provider signature analytic extracts context data indicative of the identity of the provider involved in the underlying medical claim (as indicated at Block 802), and utilizes the extracted context data to retrieve a provider signature (e.g., pre-generated provider parameter data 432, which may be indicative of the behavior of an individual provider (as indicated in FIG. 9B) or may be indicative of the behavior of an individual provider relative to other providers (as indicated in FIG. 9A)) corresponding to the provider identified as being associated with the medical claim, as indicated at Block 803. The provider signature analytic thereafter compares data elements within the common data input object against various attributes of the provider as represented within the provider signature to determine whether any attributes of the underlying medical claim are indicative of potential fraud, as indicated at Block 804. As noted above, a deviation score may be calculated for a plurality of attributes of a particular claim as compared against corresponding attributes represented within the historical data for a particular provider. Those deviation scores may then be combined and compared against past deviation scores to determine whether a particular claim is similar to a provider's historical claims. For example, a drastic change in the rate at which claims are submitted (e.g., a substantial week-over-week increase in the number of claims submitted), a drastic change in the cost of claims submitted, and/or the like (e.g., determined based at least in part on a moving average of provider-specific claims data within the pre-generated provider parameter data 432). Provider specific data may additionally enable a determination of whether actual, submitted claims are consistent with observed probable claim features over time, by utilizing a distribution of scores to measure the similarity between submitted claims and previously identified anomalous claims. As yet other examples, a determination that a particular provider's behavior differs greatly from other providers (e.g., the total number of claims is significantly lower than other providers while the total monetary value of claims collected is higher than other providers) may be indicative of potentially fraudulent behavior. Moreover, it should be noted that the compressed provider parameter data 432, as illustrated within the configuration of FIG. 4, may comprise a single data set that may be usable by a plurality of program analytics 441-444 (e.g., the FWAE scoring analytic and the provider signature analytic), or the compressed provider parameter data 432 may comprise a plurality of compressed data sets usable by respective ones of the plurality of program analytics 441-444 (e.g., a first data set usable by the FWAE scoring analytic and a second data set usable by the provider signature analytic).

The provider signature analytic is further configured to generate an output that may be populated within a common output object as discussed herein and as illustrated at Block 805 of FIG. 8. As noted above, the provider signature analytic may be configured to generate a score (e.g., a combined deviation score) and one or more reason codes providing an explanation of the generated score. For example, these reason codes may provide contextual information as to why a particular score was determined to be similar (or dissimilar) from prior claims submitted by the provider. In certain embodiments, the common output object comprises data outputs from each of a plurality of analytics executing for a particular medical claim. Thus, as discussed above in reference to the FWAE scoring analytic, the provider signature analytic may pass the generated output to a memory storage area utilized to combine data elements to be presented as a part of a combined common output object to be presented to the user 3. Provider Network Analytic In certain embodiments, the analytic platform 100 may be further configured to execute a provider network analytic providing data indicative of relationships between a plurality of providers (e.g., relationships established by shared patients, referrals, location within a common building, associations with a common entity (e.g., hospital), and/or the like). In certain embodiments, the provider network may be constructed based at least in part on graphical database entries establishing relationships between a plurality of providers, such as described U.S. Patent Publ. No. 2018/0096105, the contents of which are incorporated herein by reference in their entirety.

As shown in the schematic illustration of program analytics 441-444 of FIG. 4, the provider network analytic may comprise one or more subsystems operating in accordance with a process stream. Those subsystems may comprise an intake/detection subsystem for intaking input (e.g., the common data input object 424), extracting appropriate pre-compressed parameters for analyzing the input (e.g., from the pre-generated parameter storage area 403), and reviewing a provider network to determine whether a particular provider is associated with suspected fraudulent activity. The subsystems may further comprise a subsystem for finalizing data relating to the claim (e.g., finalizing output data by assembling an output), and a subsystem for outputting the data for ultimate inclusion within a common output object 405.

In certain embodiments, the provider network analytic is configured to generate a top-down view of relationships between a plurality of providers to identify potentially suspicious relationships therebetween. Thus, rather than focusing on relationships originating from known fraudsters, the provider network analytic is configured to review characteristics of various connections between a plurality of providers to determine whether any unusual and/or suspicious connections are established among a plurality of providers. However, it should be understood that the provider network analytic may be further configured for reviewing data indicative of known fraudsters (e.g., as indicated by publicly available data indicating fraud convictions, which may be identified automatically by a web crawler).

Figure 11:
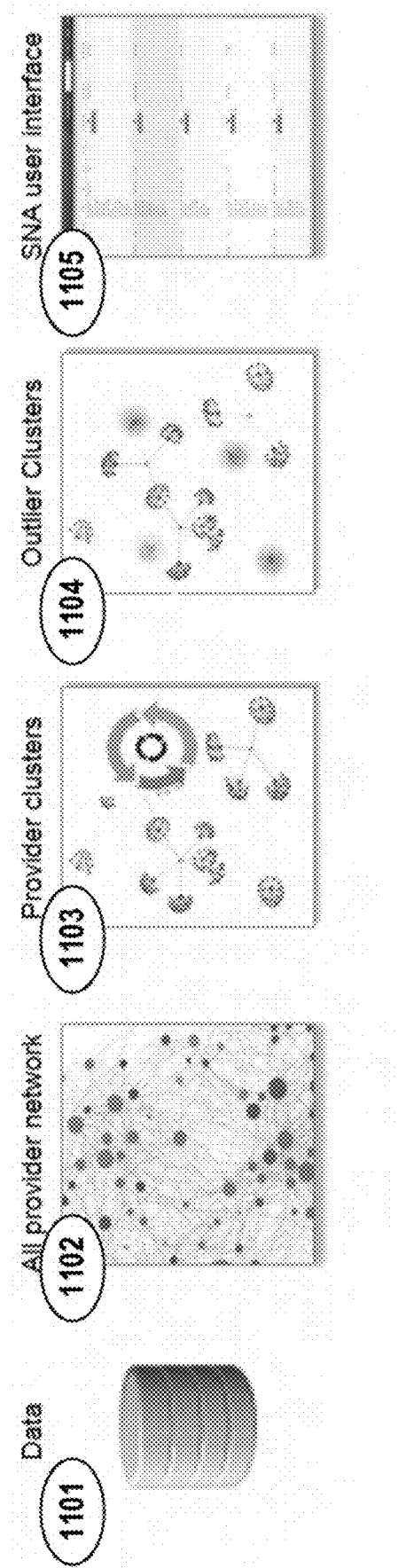
FIG. 11 graphically depicts various steps performed by a provider network analytic according to various embodiments.

In certain embodiments, the provider network encompasses an overall network of providers, wherein each provider may be presented as a node within a large interconnected network, and edges between those nodes are representative of connections between various providers. FIG. 11 provides an example illustration of various steps involved in executing a provider network analytic, which encompasses an illustration of a provider network, illustrating various connections between nodes, and illustrating tightly-concentrated subnetworks encompassing a plurality of providers. As mentioned, edges between provider nodes may indicative of shared patients, shared business addresses, and/or any other connection that may be established between a plurality of providers. The edges may be characterized by underlying data indicative of the connections between providers. Thus, an edge may be associated with data indicative of the quantity (and/or identity) of shared patients, the location of each provider, and/or any other data utilized to establish a connection between providers. Similarly, nodes within the network may be associated with provider data (e.g., provider profile data as discussed above in relation to other analytics, or other provider-specific data utilized particularly for the provider network analytic).

Based at least in part on various characteristics of the providers themselves (represented as data stored in association with provider-specific nodes) and/or based at least in part on characteristics of connections between a plurality of providers, the provider network analytic may be configured to identify subnetworks within the provider network (e.g., as illustrated in FIG. 11), wherein each subnetwork is associated with a closely related group of providers. The providers within a particular subnetwork may encompass all providers within a particular zip code, a subset of providers within a particular zip code, all providers practicing within a particular specialty, and/or the like. It should be understood that a plurality of subnetworks may be established within a single network, and in certain embodiments, those plurality of subnetworks may overlap (e.g., such that a particular provider may be classified within a plurality of subnetworks).

In certain embodiments, data indicative of the network and/or subnetwork associated with a particular provider may be compressed (e.g., such that only data indicative of the presence of connections between various providers is utilized by the provider network analytic, without reference to the underlying specifics of those connections) and may be stored within the pre-generated parameter storage area 403 (e.g., as a portion of the compressed provider parameter data 432). As with prior-described program analytics, by utilizing a compressed data set within the provider network analytic, the analytic platform 100 may execute the provider network analytic with low latency, thereby enabling real-time analyses of particular claims utilizing the compressed provider network data.

In certain embodiments, for example, the provider network analytic may be configured to identify newly formed connections that span across otherwise unconnected subnetworks (e.g., a new patient being shared between providers that were previously unconnected); a plurality of close-in-time connections being formed involving a single provider; and/or the like. Ultimately, medical claims (represented as common data input objects) relating to any of these suspicious connections (e.g., a medical claim involving a patient forming the new connection between providers; and/or the like) may be flagged as suspicious for potential follow-up by the provider network analytic. In other embodiments, providers identified as being involved in suspicious activity with other providers within a network may be flagged, such that any further claim submitted on their behalf may be reviewed in greater detail for the possibility of fraudulent behavior. Thus, the provider network analytic may be configured to provide information that may be utilized to identify potential collusive behavior between providers. For example, the provider network analytic may be configured to aid in the identification of suspicious referral patterns between providers, suspiciously similar billing patterns between providers, unusual geographical anomalies (e.g., referrals between providers located unusually far from one another) and/or the like.

Figure 10:
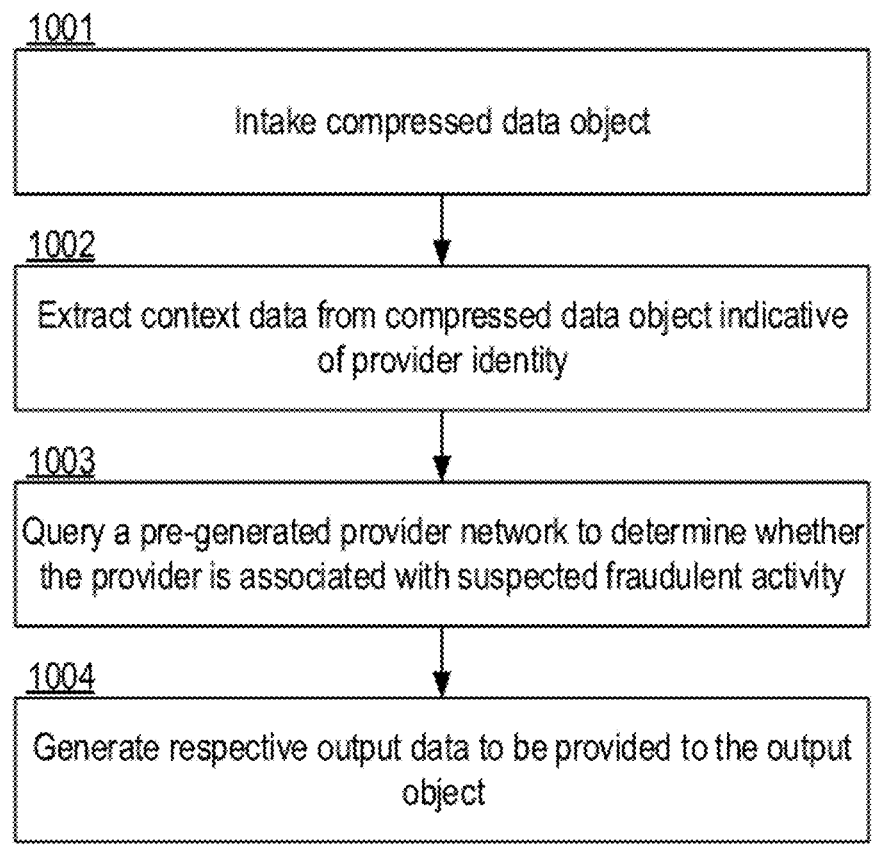
FIG. 10 illustrates a flowchart providing steps executed by a provider network analytic.

FIGS. 10-11 illustrate example steps performed by the provider network analytic according to various embodiments. In operation, the analytic platform 100 provides the common data input object to the provider network analytic, which intakes the common data input object as indicated at Block 1001 (and as reflected at 1101 of FIG. 11) and extracts context data indicative of the associated provider involved with the underlying medical claims record as indicated at Block 1002 of FIG. 10. The provider network analytic may then query a pre-generated provider network (as illustrated at 1102 of FIG. 11), as indicated at Block 1003, to identify a subnetwork associated with the provider identified from the context data. As indicated at 1103 of FIG. 11, identifying a subnetwork associated with the provider comprises identifying a plurality of provider clusters within the all-provider network. Those clusters may be identified as grouped providers having one or more similar characteristics, such as sharing a threshold number of patients therebetween, being located within the same building, being associated with the same private membership group, being located within the same zip code, and/or the like.

Moreover, of the identified provider clusters, the analytic computing entity is configured to identify outlier clusters, as indicated at 1104 of FIG. 11. Outlier clusters may be identified based at least in part on summary characteristics that are indicative of unusual behavior of providers within those clusters that may be compared against other clusters having similar characteristics. For example, those outlier clusters may be identified has having an abnormally high average number of billings per provider versus other clusters, and/or the like.

In certain embodiments, the provider network analytic may determine whether the provider has been flagged for follow-up based at least in part on prior-identified suspicious activity (e.g., data indicative of such flags may be represented within the compressed provider network data), and/or the provider network analytic may be configured to determine whether the underlying claim associated with the common data input object is associated with suspicious behavior by one or more providers.

Ultimately, the provider network analytic is configured to generate an output as indicated at Block 1004 (e.g., indicative of any flags associated with the provider, flags associated with the claim itself, and/or the like), which may be embodied as a user interface as indicated at 1105 of FIG. 11. The generated user interface may graphically depict relationships between various providers within identified outlier clusters as a graphical network, with individual nodes of the generated graphical network representing individual providers, and edges between those individual nodes representing relationships between providers. The graphical user interface may be highly interactive, allowing users to probe individual nodes and/or edges to obtain additional information about the providers or relationships identified between providers. This output may be presented together with the output of other analytics executing via the analytic platform 100 as discussed throughout this description. Thus, as discussed above in reference to the FWAE scoring analytic, and the provider signature analytic, the provider network analytic may pass the generated output to a memory storage area utilized to combine data elements to be presented as a part of a common output object to be presented to the user.

4. Historical Medical Record Analytic

In certain embodiments, the analytic platform 100 is further configured to compare a particular claim (as represented by the common data input object) against a historical data record generated and/or maintained by the historical medical record analytic and indicative of a history of past medical claims. By comparing data elements of the common data input object 424 against the historical medical record in accordance with a defined algorithm executed via the analytic, the analytic determines whether the underlying medical claim represented by the common data input object is consistent with the patient's historical medical record, which is indicative of a history of past claims relating to the patient. A determination that the data elements of the common data input object is inconsistent with the patient's historical medical record may cause the analytic to provide an output recommending that further investigation is warranted into the claim.

As shown in the schematic illustration of program analytics 441-444 of FIG. 4, the historical medical record analytic may comprise one or more subsystems operating in accordance with a process stream. Those subsystems may comprise an intake/detection subsystem for intaking input (e.g., the common data input object 424), extracting appropriate pre-compressed parameters for analyzing the input (e.g., extracting historical medical records from the pre-generated parameter storage area 403, such as from the compressed patient parameter data 431), and detecting whether the common data input object 424 is indicative of the presence of fraud. The subsystems may further comprise a subsystem for finalizing data relating to the claim (e.g., finalizing output data by assembling an output), and a subsystem for outputting the data for ultimate inclusion within a common output object 405.

In certain embodiments, the historical medical record analytic may be configured to utilize a derived medical record generated based at least in part on historical claims data relevant for a particular patient that is accessible to the analytic platform 100 (or another platform configured to generate such a derived medical record). Various methodologies utilized for generating a derived medical record are described in detail in U.S. Patent Publ. No. 2015/0332003, the contents of which are incorporated herein by reference in their entirety. In such embodiments, the analytic platform 100 is configured to make an initial determination of whether a particular claim is consistent with the patient's medical history and whether a particular medical claim and the performed medical procedure codes are consistent, without separately requesting official medical records for the patient. In other embodiments, the historical medical record analytic is configured to utilize a patient's complete medical record while analyzing the data elements of the common data input object to determine whether a particular claim is consistent with the patient's historical medical record.

In embodiments utilizing a patient's derived medical record, the derived medical record may be embodied as compressed data indicative of historical claims involving the patient. Accordingly, the historical medical record analytic may be configured to utilize the compressed data of the derived medical record in combination with the common data input object to determine whether the underlying medical claim is consistent with the patient's medical history.

Figure 12:
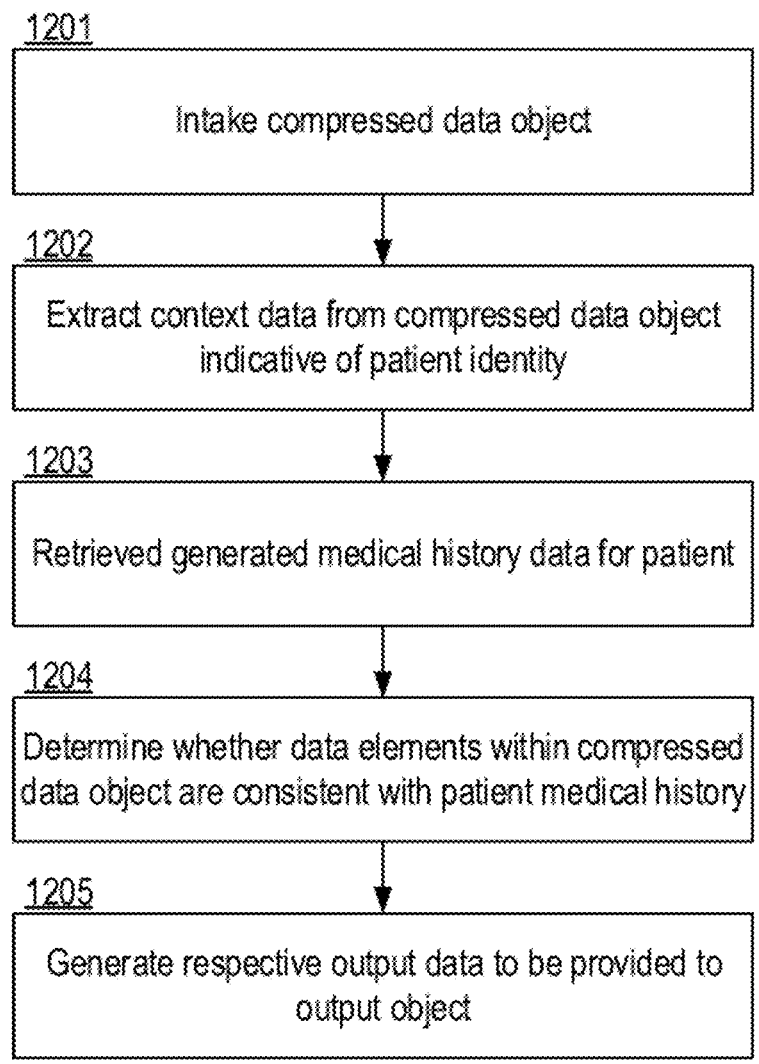
FIG. 12 is a flowchart providing steps executed by a historical medical record analytic.

FIG. 12 provides an illustrative summary of steps performed by the historical medical record analytic. As shown at Block 1201, the historical medical record analytic intakes a common data input object 424 for analysis according to various embodiments. The historical medical record analytic then extracts context data from the common data input object 424, as indicated at Block 1202, to identify a patient associated with the underlying medical claim. The historical medical record analytic then retrieves a corresponding medical record for the patient (e.g., a compressed derived medical record stored within the pre-generated parameter storage area 403, such as within the compressed patient parameter data 431) as indicated at Block 1203, and determines whether data elements of the common data input object 424 are consistent with the patient's medical history, as indicated at Block 1204. Moreover, the historical medical record analytic may review the contents of the common data input object 424 for internal consistency as well, by determining whether a particular medical claim (e.g., indicative of a condition, disease, virus, symptom, and/or the like) is consistent with a procedure performed on the patient (e.g., identified based at least in part on a unique procedure code). A determination that a particular procedure code was entirely irrelevant to a particular condition of the patient may be indicative of fraud, warranting further investigation. For example, for a medical claim relating to a broken femur, a procedure code relating to implanting a heart stent would be entirely irrelevant, and may warrant further investigation to determine whether the procedure was indicative of the occurrence of fraud.

The historical medical record analytic may be configured to generate an output indicative of whether further investigation is necessary to determine whether the underlying claim is consistent with the patient's medical history, as indicated at Block 1205. Thus, the output may provide a data output providing a recommendation to pull a patient's full medical record for further investigation, or whether the patient's full medical record is unnecessary to determine that the claim is consistent with the patient's medical history (e.g., the data output may be embodied as a textual data output—a "pull" output may recommend that the patient's medical records should be pulled for further investigation, and a "don't pull" output may recommend that the patient's medical records need not be pulled for further investigation).

As mentioned above, this output may be presented together with the output of other analytics executing via the analytic platform 100 as discussed throughout this description. Thus, as discussed above in reference to the FWAE scoring analytic, the provider signature analytic, and the provider network analytic, the historical medical history analytic may pass the generated output to a memory storage area utilized to combine data elements to be presented as a part of a combined common output object 405 to be presented to the user.

c. Operations Layer

As mentioned above, the analytic platform 100 is configured to generate a common output object 405 in certain embodiments to be utilized during operations layer processing. The common output object 405 comprises outputs received from each of the program analytics 441-444 executed by the analytic platform 100. As mentioned above, the program analytics 441-444 execute in parallel, such that outputs from each of the program analytics 441-444 may be combined in memory at least substantially simultaneously. The analytic platform 100 is configured to generate an common output object 405 to be presented to a user (e.g., via a display of a user computing entity 30), based at least in part on the outputs from each of the program analytics 441-444 as stored in the memory. Moreover, in certain embodiments, the common output object 405 may be generated based at least in part on formatting requirements (e.g., as defined within a separate formatting file stored in memory) for presentation to the user.

In various embodiments, the common output object 405 may comprise one or more hyperlinks to initiate operations layer processing, for example, to undertake further analysis of a particular medical claim underlying the common data input object 424 consumed by each of the analytics. For example, the common output object 405 may comprise hyperlinks to cause a user computing entity 30 displaying the common output object 405 to generate a request for the original 837 claim record 401 utilized for generating the common data input object 424. Moreover, the common output object 405 may comprise hyperlinks that cause the user computing entity 30 to request a patient's full medical record. As yet another example, the common output object 405 may comprise hyperlinks to cause the user computing entity 30 to request access to a graphical display of a provider network (e.g., similar to that shown in FIG. 11). As yet another example, the common output object 405 may comprise hyperlinks to cause the user computing entity 30 to triage a request to the analytic platform 100 to initiate a full investigation process for a particular medical claim. That investigation process may subsequently initiate one or more computing processes and/or may generate alerts to be transmitted to one or more additional user computing entities 30 requesting other individuals to perform one or more investigatory actions of the particular claim.

In various embodiments, the common output object 405 may be stored in a database for later retrieval. In certain embodiments, the common output object 405 may be stored with one or more links associating the common output object 405 with the patient, the provider, an entity associated with the provider, the original 837 data record 401, the common data input object 424, and/or the like. Moreover, in various embodiments the common output object 405 may be available to additional systems via an Application Program Interface (API) that enables data to be passed to other systems. As a specific example, the common output object 405 may be passed to a separate investigation system for initializing a more detailed investigation of a particular medical claim.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An analytic platform for processing a claim record, the analytic platform comprising one or more memory storage areas and one or more processors configured to:
   receive a record data file;
   compress the record data file to generate a common data input object comprising a plurality of data elements, wherein each data element of the plurality of data elements represents one or more attributes of the record data file;
   provide the common data input object as input to each of a plurality of program analytics executing independently and in parallel on the analytic platform, and wherein:
   (a) each of the plurality of program analytics independently retrieves at least one compressed parameter file from a plurality of compressed parameters files for use in processing data elements of the common data input object, wherein (1) the at least one compressed parameter file retrieved by the corresponding program analytic of the plurality of program analytics is based at least in part on a data element of the common data input object, and (2) the at least one compressed parameter file comprises a plurality of compressed parameters, and
   (b) each of the plurality of program analytics is configured to generate a respective output based at least in part on (1) one or more of the plurality of data elements of the common data input object, and (2) at least one compressed parameter of the plurality of compressed parameters from the corresponding at least one compressed parameter file, such that the plurality of program analytics is configured to collectively generate a plurality of respective outputs; and
   combine the plurality of respective outputs collectively generated by the plurality of program analytics into a common output object.

2. The analytic platform of claim 1, wherein the one or more processors are further configured to:
   receive historical data files relating to an actor identified within the record data file;
   compress the one or more historical data files to generate a historical summary data file relating to the actor; and
   wherein the at least one compressed parameter file retrieved by the corresponding program analytic of the plurality of program analytics is embodied as the historical summary data file relating to the actor.

3. The analytic platform of claim 1, wherein the plurality of analytics comprise one or more of:

a fraud, waste, abuse, and error (FWAE) scoring analytic;
a provider signature analytic;
a provider network analytic; or
a historical medical record analytic.

4. The analytic platform of claim 1, wherein the plurality of program analytics comprises a fraud, waste, abuse, and error (FWAE) scoring analytic, and wherein the FWAE scoring analytic is configured to:
 parse the common data input object to identify one or more contexts relating to an underlying claim record;
 retrieve at least one compressed parameter file relating to each of the identified one or more contexts; and
 generate an output comprising a score value for the common data input object.

5. The analytic platform of claim 4, wherein the FWAE scoring analytic is further configured to generate a human-readable narrative corresponding to the score value.

6. The analytic platform of claim 4, wherein the one or more contexts relating to the underlying claim record comprise one or more of: a patient identity, a provider identity, an entity identity, or a medical claim.

7. The analytic platform of claim 4, wherein the at least one compressed parameter file is generated periodically based at least in part on historical data relating to a respective context of the one or more contexts.

8. The analytic platform of claim 7, wherein the historical data is embodied as historical data generated during a moving time period having a defined length.

9. The analytic platform of claim 1, wherein the plurality of program analytics comprises a provider signature analytic, and wherein the provider signature analytic is configured to:
 parse the common data input object to identify a provider relating to an underlying claim record;
 retrieve a compressed parameter file comprising historical data relating to the provider; and
 generate an output identifying whether data elements within the common data input object are consistent with the compressed parameter file.

10. A method for processing a claim record via an analytic platform, the method comprising:
 receiving, by the analytic platform, a record data file;
 compressing, by the analytic platform, the record data file to generate a common data input object comprising a plurality of data elements, wherein each data element of the plurality of data elements represents one or more attributes of the record data file;
 providing, by the analytic platform, the common data input object as input to each of a plurality of program analytics executing independently and in parallel on the analytic platform, and wherein:
  (a) each of the plurality of program analytics independently retrieves at least one compressed parameter file from a plurality of compressed parameters files for use in processing data elements of the common data input object, wherein (1) the at least one compressed parameter file retrieved by the corresponding program analytic of the plurality of program analytics is based at least in part on a data element of the common data input object, and (2) the at least one compressed parameter file comprises a plurality of compressed parameters, and
  (b) each of the plurality of program analytics is configured to generate a respective output based at least in part on (1) one or more of the plurality of data elements of the common data input object, and (2) at least one compressed parameter of the plurality of compressed parameters from the corresponding at least one compressed parameter file, such that the plurality of program analytics is configured to collectively generate a plurality of respective outputs; and
 combining, by the analytic platform, the plurality of respective outputs collectively generated by the plurality of program analytics into a common output object.

11. The method for processing a claim record of claim 10, further comprising:
 receiving historical data files relating to an actor identified within the record data file;
 compressing the one or more historical data files to generate a historical summary data file relating to the actor; and
 wherein the at least one compressed parameter file retrieved by the corresponding program analytic of the plurality of program analytics is embodied as the historical summary data file relating to the actor.

12. The method for processing a claims record of claim 10, wherein the plurality of analytics comprise one or more of:
 a fraud, waste, abuse, and error (FWAE) scoring analytic;
 a provider signature analytic;
 a provider network analytic; or
 a historical medical record analytic.

13. The method for processing a claim record of claim 10, wherein the plurality of program analytics comprises a fraud, waste, abuse, and error (FWAE) scoring analytic, and wherein the FWAE scoring analytic is configured to:
 parse the common data input object to identify one or more contexts relating to an underlying claim record;
 retrieve at least one compressed parameter file relating to each of the identified one or more contexts; and
 generate an output comprising a score value for the common data input object.

14. The method for processing a claim record of claim 13, wherein the one or more contexts relating to the underlying claim record comprise one or more of: a patient identity, a provider identity, an entity identity, or a medical claim.

15. The method for processing a claim record of claim 10, wherein the plurality of program analytics comprises a provider signature analytic, and wherein the provider signature analytic is configured to:
 parse the common data input object to identify a provider relating to an underlying claim record;
 retrieve a compressed parameter file comprising historical data relating to the provider; and
 generate an output identifying whether data elements within the common data input object are consistent with the compressed parameter file.

16. A computer program product comprising a non-transitory computer readable medium having computer program instructions stored therein, the computer program instructions when executed by a processor, cause an analytic platform to:
 receive a record data file;
 compress the record data file to generate a common data input object comprising a plurality of data elements, wherein each data element of the plurality of data elements represents one or more attributes of the record data file;
 provide the common data input object as input to each of a plurality of program analytics executing independently and in parallel on the analytic platform, and wherein:

(a) each of the plurality of program analytics independently retrieves at least one compressed parameter file from a plurality of compressed parameters files for use in processing data elements of the common data input object, wherein (1) the at least one compressed parameter file retrieved by the corresponding program analytic of the plurality of program analytics is based at least in part on a data element of the common data input object, and (2) the at least one compressed parameter file comprises a plurality of compressed parameters, and (b) each of the plurality of program analytics is configured to generate a respective output based at least in part on (1) one or more of the plurality of data elements of the common data input object, and (2) at least one compressed parameter of the plurality of compressed parameters from the corresponding at least one compressed parameter file, such that the plurality of program analytics is configured to collectively generate a plurality of respective outputs; and combine the plurality of respective outputs collectively generated by the plurality of program analytics into a common output object.

17. The computer program product of claim 16, wherein the computer program instructions when executed by a processor, cause the processor to:

receive historical data files relating to an actor identified within the record data file;

compress the one or more historical data files to generate a historical summary data file relating to the actor; and wherein the at least one compressed parameter file retrieved by the corresponding program analytic of the plurality of program analytics is embodied as the historical summary data file relating to the actor.

18. The computer program product of claim 16, wherein the plurality of analytics comprise one or more of:

a fraud, waste, abuse, and error (FWAE) scoring analytic;
a provider signature analytic;
a provider network analytic; or
a historical medical record analytic.

19. The computer program product of claim 16, wherein the plurality of program analytics comprises a fraud, waste, abuse, and error (FWAE) scoring analytic, and wherein the FWAE scoring analytic is configured to:

parse the common data input object to identify one or more contexts relating to an underlying claim record;

retrieve at least one compressed parameter file relating to each of the identified one or more contexts; and generate an output comprising a score value for the common data input object.

20. The computer program product of claim 16, wherein the plurality of program analytics comprises a provider signature analytic, and wherein the provider signature analytic is configured to:

parse the common data input object to identify a provider relating to an underlying claim record;

retrieve a compressed parameter file comprising historical data relating to the provider; and generate an output identifying whether data elements within the common data input object are consistent with the compressed parameter file.

* * * * *

UNITED STATES PATENT AND TRADEMARK OFFICE
CERTIFICATE OF CORRECTION

PATENT NO. : 11,605,449 B2
APPLICATION NO. : 17/450631
DATED : March 14, 2023
INVENTOR(S) : Chris Celka et al.

Page 1 of 1

It is certified that error appears in the above-identified patent and that said Letters Patent is hereby corrected as shown below:

In the Claims

In Column 32, Line 21, Claim 12, delete "claims record" and insert -- claim record --, therefor.

Signed and Sealed this
Sixth Day of June, 2023

Katherine Kelly Vidal
*Director of the United States Patent and Trademark Office*